US009758837B2

(12) United States Patent
Duan et al.

(10) Patent No.: US 9,758,837 B2
(45) Date of Patent: Sep. 12, 2017

(54) **SENSITIVE AND RAPID METHOD FOR *CANDIDATUS LIBERIBACTER* SPECIES DETECTION**

(71) Applicants: The United States of America, as represented by the Secretary of Agriculture, Washington, DC (US); University of Florida Research Foundation, Inc., Gainesville, FL (US)

(72) Inventors: Yong Duan, Fort Pierce, FL (US); Lijuan Zhou, Fort Pierce, FL (US); John Kent Morgan, Port Saint Lucie, FL (US)

(73) Assignees: The United States of America, as represented by the Secretary of Agriculture, Washington, DC (US); University of Florida Research Foundation, Gainesville, FL (US)

( * ) Notice: Subject to any disclaimer, the term of this patent is extended or adjusted under 35 U.S.C. 154(b) by 601 days.

(21) Appl. No.: 14/073,205

(22) Filed: Nov. 6, 2013

(65) Prior Publication Data
US 2015/0126383 A1 May 7, 2015
US 2016/0153027 A9 Jun. 2, 2016

Related U.S. Application Data

(62) Division of application No. 13/564,957, filed on Aug. 2, 2012, now abandoned.

(60) Provisional application No. 61/514,315, filed on Aug. 2, 2011.

(51) Int. Cl.
*C12Q 1/68* (2006.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,237,224 A | 12/1980 | Cohen et al. | |
| 4,889,818 A | 12/1989 | Gelfand et al. | |
| 5,079,352 A | 1/1992 | Gelfand et al. | |
| 5,210,015 A | 5/1993 | Gelfand et al. | |
| 5,310,652 A | 5/1994 | Gelfand et al. | |
| 5,322,770 A | 6/1994 | Gelfand | |
| 5,338,671 A | 8/1994 | Scalice et al. | |
| 5,407,800 A | 4/1995 | Gelfand et al. | |
| 5,436,134 A | 7/1995 | Haugland et al. | |
| 5,487,972 A | 1/1996 | Gelfand et al. | |
| 5,538,848 A | 7/1996 | Livak et al. | |
| 5,587,287 A | 12/1996 | Scalice et al. | |
| 5,618,711 A | 4/1997 | Gelfand et al. | |
| 5,658,751 A | 8/1997 | Yue et al. | |
| 5,677,152 A | 10/1997 | Birch et al. | |
| 5,723,591 A | 3/1998 | Livak et al. | |
| 5,773,258 A | 6/1998 | Birch et al. | |
| 5,789,224 A | 8/1998 | Gelfand et al. | |
| 5,804,375 A | 9/1998 | Gelfand et al. | |
| 5,876,930 A | 3/1999 | Livak et al. | |
| 5,994,056 A | 11/1999 | Higuchi | |
| 6,030,787 A | 2/2000 | Livak et al. | |
| 6,127,155 A | 10/2000 | Gelfand et al. | |
| 6,171,785 B1 | 1/2001 | Higuchi | |
| 6,258,569 B1 | 7/2001 | Livak et al. | |
| 6,814,934 B1 | 11/2004 | Higuchi | |
| 2014/0045191 A1* | 2/2014 | DeJohn | C12Q 1/686 435/6.12 |
| 2015/0093755 A1 | 4/2015 | Zhao et al. | |

OTHER PUBLICATIONS

Zhou et al. (Diversity and plasticity of the intracellular plant pathogen and insect symbiont, 'Candidatus Liberibacter asiaticus', revealed by hyper variable prophage genes with intragenic tandem repeats, Appl Environ Microbiol, Sep. 2011;77(18):6663-73, Epub Jul. 22, 2011).*

Benson, G., "Tandem repeats finder: a program to analyze DNA sequences" (1999) Nucleic Acid Research 27(2): 573-580.

De Barro, P. J. and F. Driver, "Use of RAPD PCR to Distinguish the B Biotype from Other Biotypes of Bemisia tabaci" (1997) Australian Journal of Entomology 36: 149-152.

Duan, Yongping et al., "Complete Genome Sequence of Citrus Huanglongbing Bacterium, 'Candidatus Liberibacter asiaticus' Obtained Through Metagenomics", (2009) Molecular Plant-Microbe Interactions 22(8): 1011-1020.

Hung, T.H. et al., "Detection by PCR of Candidatus Liberibacter asiaticus, the bacterium causing citrus huanglongbing in vector psyllids: application to the study of vector-pathogen relationships" (2004) Plant Pathology 53: 96-102.

Kim, J.-S., et al., "Response of Sweet Orange (*Citrus sinensis*) to 'Candidatus Liberibacter asiaticus' Infection: Microscopy and Microarray Analyses" (2009) Phytopathology 99(1): 50-57.

Li, W., J. S. Hartung, L. Levy, "Quantitative real-time PCR for detection and identification of *Candidatus* Liberibacter species associated with citrus huanglongbing" (2006) Journal of Microbiological Methods 66: 104-115.

Li W. et al., "Evaluation of DNA Amplification Methods for Improved Detection of *Candidatus* Liberibacter Species Associated with Citrus Huanglongbing" (2007) Plant Disease 91(1): 51-58.

Li, W. et al., "Optimized Quantification of Unculturable *Candidatus* Liberibacter Spp. in Host Plants Using Real-Time PCR" (2008) Plant Disease 92(6): 854-861.

Li, W. et al., "Quantitative Distribution of Candidatus Liberibacter asiaticus in Citrus Plants with Citrus Huanglongbing" (2009) Phytopathology 99(2): 139-144.

(Continued)

*Primary Examiner* — Aaron Priest
(74) *Attorney, Agent, or Firm* — John D. Fado; David L. Marks

(57) ABSTRACT

DNA amplification methods using primers obtained from the genes $hyv_I$ and $hyv_{II}$ from the *Candidatus Liberibacter asiaticus* genome are useful for detecting Ca. L. species in plants and insect hosts.

10 Claims, 10 Drawing Sheets

(56) References Cited

OTHER PUBLICATIONS

Teixeira, D. C. et al., "Distribution and quantification of Candidatus Liberibacter americanus, agent of huanglongbing disease of citrus in Sao Paulo State, Brasil, in leaves of an affected sweet orange tree as determined by PCR" (2008) Molecular and Cellular Probes 22: 139-150.
Wang, Z. et al., "Development and application of molecular-based diagnosis for 'Candidatus Liberibacter asiaticus', the causal pathogen of citrus huanglongbing" (2006) Plant Pathology 55: 630-638.
Zhou, L. et al., "Diversity and Plasticity of the Intracellular Plant Pathogen and Insect Symbiont "Candidatus Liberibacter asiaticus" as Revealed by Hypervariable Prophage Genes with Intragenic Tandem Repeats" (2011) Applied and Environmental Microbiology 77(18): 6663-6673.
Duan et al. Complete Genome Sequence of Citrus Huanglongbing Bacterium, 'Candidatus Liberibacter asiaticus' Obtained Through Metagenomics, MPMI vol. 22, No. 8, pp. 1011-1020 (Aug. 2009).
NCBI Accession No. CP001677 (submitted Jul. 13, 2009).
Zhou et al. (Diversity and plasticity of the Intracellular plant pathogen and insect symbiont, 'Candidatus Liberibacter asiaticus', revealed by hyper variable prophage genes with intragenic tandem repeats, Appl Environ Microbiol, Sep. 2011; 77(18):6663-73, Epub Jul. 22, 2011).
NCBI Accession No. HQ263703 (submitted Sep. 16, 2010).
Stratagene (Gene Characterization Kits; 1988).
NCBI Gi. 254039798 (attached; available Jul. 17, 2009).
Didenko (Fluorescent Energy Transfer Nucleic Acid Probes, Humana Press, 2006).
Nallamsetty et al. (A generic protocol for the expression and purification of recombinant proteins in *Escherichia coli* using a combinatorial His6-maltose binding protein fusion tag, Nature Protocols, vol. 2, No. 2, pp. 383-391 2007).
Keremane, Manjunath L. et al., "A rapid field detection system for citrus huanglongbing associated 'Candidatus Liberibacter asiaticus' from the psyllid vector, Diaphorina citri Kuwayama and its implications in disease management" (2015), Crop Protection 68:41-48.
Kogenaru, S. et al., "Repertoire of novel sequence signatures for the detection of Candidatus Liberibacter asiaticus by quantitative real time-PCR", (2014) Journal of Citrus Patology 1:94-95.
Nageswara-Rao, Madhugiri et al., "Development of rapid, sensitive and non-radioactive tissue-blot diagnostic method for the detection of citrus greening", (2013), Molecular and Cellular Probes 27:176-183.
Zhang, Shujian et al., "'Ca. Liberibacter asiaticus' Carries an Excision Plasmid Prophage and a Chromosomally Integrated Prophage That Becomes Lytic in Plant Infections", (2011), MPMI 24(4):458-468.

* cited by examiner

**pLJ153.1 *hyv*I gene sequence (single repeat): 1164 b (excerpt) SEQ ID NO.: 24**

```
ATGATTAGAAAAGTAAACATGGAAAAACTAAACTTCGAACAAACTAAATCGGTTACCTAT
TGGGCTGTAGGATCAAAGTTTGTCATTCCTTGGGATATTAAAGATCCAAGTAGGATTCAT
GCTGAAGTTGGATATTCCGATGGAAGAGTTCAAGAACTAGCAATATCCCAAGATTTTGAT
GTCGATGGGTTAAACGCTTTGCTAACTGTCAACAATAGAGAAGGGGATTTTATCCGTATT
TTCGAAGGTGAGAAACAAACTTTTAAAGAATATAACTCTGATAGCCCCAGAGCTCCTCAT
AATCTTGTTAAAGAAGCGGATTTGTATCCTTTGCATAATAGATTAGATGGTGTTGAAACT
ATCGTTTCTGATCTTAACAATATGAAAAACAGGATCCAAGAACTAGAACAAATTGATTTA
TCTAAACTAGAACAAATTGATTTATCTGAAATGGCCGTTTTAACACAAAAGATGAATATC
GTAGATGGAAGAGTCAATGATCTAGCTACTCAAACGAAAGATGTTGGTCGTAAACTAGAA
CAAATTGATTTATCTAAACTAGAAGGTTTAGATCCACAAACACGAAAGTATCTACAAGAT
ATACAAACGCAGTTAACGTCGGATACGCTCACGCTTCAACATGAGGACACTAGAAGGTAT
GCTTCATCTATAAGTTTCAAGGGTAACGATGGGGCACTAGTTGGTTGGATCACGAGAGAG
GTTATAGGGGATCTTAAGGGTCTATCCATAGCAACAAAGAATCAGAGCGGAAGCCTTGTA
AATAGTGTTAAACTCTATGACAACATGGATGTCTATATCCAAGGTCAGTGTTTCATTAGG
GGAACTGATACCTCTATCTTTGATGAAATAAAACGACAACTAAAACCTTATATTCTAGGT
TTGCTCCAAGGGCGTACAATGGTACGAAGTGCCAATCTACGTGAAAAAGCTTCAATTGGT
GATATAATAACAGGGGATAAAATAGACTATTGGGCTTATCCTTCAGAAAACGGCAGTGGT
TATATATCAGCTAGTGCTACTCAAGCACACACAATGGCAGTTAGTGCAGAAGACGCACGT
AAAAGATGGAGGATTATGGGTATAACTAGAAGTTATTACTACACAGGGTATTGGTTACAA
GAAGTTATTAATTTTGATGACTAA
```

Fig. 5

**pLJ108.1 *hyvI* gene sequence (full repeat): 2760 b (excerpt) SEQ ID NO 25**

ATGATTAGAAAAGTAAACATGGAAAAACTAAACTTCGAACAAACTAAATCGGTTACCTAT
TGGGCTGTAGGATCAAAGTTTGTCATTCCTTGGGATATTAAAGATCCAAGTAGGATTCAT
GCTGAAGTTGGATATTCCGATGGAAGAGTTCAAGAACTAGCAATATCCCAAGATTTTGAT
GTCGATGGGTTAAACGCTTTGCTAACTGTCAACAATAGAGAAGGGGATTTTATCCGTATT
TTCGAAGGTGAGAAACAAACTTTTAAAGAATATAACTCTGATAGCCCCAGAGCTCCTCAT
AATCTTGTTAAAGAAGCGGATTTGTATCCTTTGCATAATAGATTAGATGGTGTTGAAACT
ATCGTTTCTGATCTTAACAATATGAAAAACAGGATCCAAGAACTAGAACAAATTGATTTA
TCTAAACTAGAACAAATTGATTTATCTAAAATGGCCGTTTTAACACAAAAGATGAATATC
ATAGATGGGGTAGTCAAGGATCTAGCTACTCAAACGAAAGATGTTGGTCGTAAACTAGAA
CAAATTGATGTATCTAAACTAGAACAAATTGATTTATCTAAAATGGCCGTTTTAACACAA
AAGATGAATATCGTAGATGGAAGAGTCAATGATCTAGCTACTCAAACGAAAGATGTTGGT
CGTAAACTAGAACAAATTGATTTATCTAAACTAGAACAAATTGATTTATCTGAAATGGCC
GTTTTAACACAAAAGATGAATATCATAGATGGGATAGTCAATAATCTAGCTACTCAAACG
GAAGATGTTGGTCGTAAACTAGAACAAATTGATTTATCTAAACTAGAACAAATTGATTTA
TCTGAAATGGCCGTTTTAACACAAAAGATGAATATCATAGATGGGATAGTCAATAATCTA
GCTACTCAAACGGAAGATGTTGGTCGTAAACTAGAACAAATTGATTTATCTAAACTAGAA
CAAATTGATTTATCTGAAATGGCCGTTTTAACACAAAAGATGAATATCATAGATGGGATA
GTCAATAATCTAGCTACTCAAACGAAAGATGTTGGTCGTAAACTAGAACAAATTGATTTA
TCTAAACTAGAACAAATTGATTTATCTGAAATGGCCGTTTTAACACAAAAGATGAATATC
ATAGATGGGATAGTCAATAATCTAGCTACTCAAACGAAAGATGTTGGTCGTAAACTAGAA
CAAATTGATTTATCTAAACTAGAACAAATTGATTTATCTAAACTAGAACAAATTGATTTA
TCTAAACTAGAACAAATTGATTTATCTGAAATGGCCGTTTTAACACAAAAGATGAATATC
ATAGATGGGATAGTCAATGATCTAGCTACTCAAACGGAAGTTGTTGGTCGTAAACTAGAA
CAAATTGATTTATCTAAACTAGAACAAATTGATTTATCTGAAATGGCCGTTTTAACACAA
AAGATGAATATCATAGATGGGATAGTCAATAATCTAGCTACTCAAACGAAAGATGTTGGT
CGTAAACTAGAACAAATTGATTTATCTAAACTAGAACAAATTGATTTATCTAAACTAGAA
CAAATTGATTTATCTAAACTAGAACAAATTGATTTATCTGAAATGGCCGTTTTAACACAA
AAGATGAATATCATAGATGGGATAGTCAATGATCTAGCTACTCAAACGGAAGTTGTTGGT
TGTAAACTAGAACAAATTGATTTATCTAAACTAGAACAAATTGATTTATCTGAAATGGCC
GTTTTAACACAAAAGATGAATATCATAGATGGGATAGTCAATAATCTAGCTACTCAAACG
AAAGATGTTGGTCGTAAACTAGAACAAATTGATTTATCTAAACTAGAACAAATTGATTTA
TCTAAACTAGAACAAATTGATTTATCTAAACTAGAACGAATTGATTTATCTGAAATGGCC
GTTTTAACACAAAAGATGAATATCGTAGATGGAATAGTCAATGATCTAGCTACTCAAACG
GAAGTTGTTGGTCGTAAGCTAGAACAAATTGATTTATCTAAACTAGAACAAATTGATTTA
TCTGAAATGGCCGTTTTAACACAAAAGATGAATATCGTAGATGGAAGAGTCAATGATCTA
GCTACTCAAACGAAAGATGTTGGTCGTAAACTAGAACAAATTGATTTATCTAAACTAGAA
GGTTTAGATCCACAAACACGAAAGTATCTACAAGATATACAAACGCAGTTAACGTCGGAT
ACGCTCACGCTTCAACATGAGGACACTAGAAGGTATGCTTCATCTATAAGTTTCAAGGGT
AACGATGGGGCACTAGTTGGTTGGATCACGAGAGAGGTTATAGGGGATCTTAAGGGTCTA
TCCATAGCAACAAAGAATCAGAGCGGAAGCCTTGTAAATAGTGTTAAACTCTATGACAAC
ATGGATGTCTATATCCAAGGTCAGTGTTTCATTAGGGGAACTGATACCTCTATCTTTGAT
GAAATAAAACGACAACTAAAACCTTATATTCTAGGTTTGCTCCAAGGGCGTACAATGGTA
CGAAGTGCCAATCTACGTGAAAAAGCTTCAATTGGTGATATAATAACAGGGGATAAAATA
GACTATTGGGCTTATCCTTCAGAAAACGGCAGTGGTTATATATCAGCTAGTGCTACTCAA
GCACACACAATGGCAGTTAGTGCAGAAGACGCACGTAAAGATGGAGGATTATGGGTATA
ACTAGAAGTTATTACTACACAGGGTATTGGTTACAAGAAGTTATTAATTTTGATGACTAA

Fig. 6 pLJ396.2 hyvII gene sequence 1371bp SEQ ID NO: 30

ATGATGCAATATAACTTCGAGCAATCGAAAGATGTGTCTTATCGTCTTTTTGGCTCTTAT
TTTGTTATTCCTTGGACTGTTAAAGATCCAAGTAGGATTCATGCTGAAGTTAAATATCCT
GATGGCAACATGGAAGAATTAAGTCCTGAAAGAGATTTTAAAGTTGATGTAGACGAAAGC
AGTTTGATTTTAAGTTCTAAAAGGTGGATTAACAATAATAACGCTTTAAGGATTTTCGAA
GGTGAGAAACAAACTTTTAAAGATTTTAACATAGAGGTACAAAAGAAAGTAAATCAGGTA
AACGTTTTAACACAAAAGATGAATACCATAGATGGGATAGTCAATGATCTAGCTACTCAA
ACGAAAGATGTTGGTCGTAAACTAGAACAAATTGATTTATCTAAACTAGAACAAATTGAT
TTATCTAAACTAGAACAAATTGATTTATCTAAACTAGAACAAATTGATTTATCTGAAATG
GCCGTTTTAACACAAAAGATGAATATCATAGATGGGATAGTCAATGATCTAGCTACTCAA
ACGGAAGTTGTTGGTCGTAAACTAGAACAAATTGATTTATCTAAACTAGAACAAATTGAT
TTATCTGAAATGGCCGTTTTAACACAAAAGATGAATATCATAGATGGGATAGTCAATAAT
CTAGCTACTCAAACGAAAGATGTTGGTCGTAAACTAGAACAAATTGATTTATCTAAACTA
GAACAAATTGATTTATCTAAACTAGAACAAATTGATTTATCTAAACTAGAAGGTTTAGAT
CCACAAACACGAAAGTATCTACAAGATATACAAACGCAGTTAACGTCGGATACGCTCACG
CTTCAACATGAGGACACTAGAAGGTATGCTTCATCTATAAGTTTCAAGGGTAACGATGGG
GCACTAGTTGGTTGGATCACGAGAGAGGTTATAGGGGATCTTAAGGGTCTATCCATAGCA
ACAAAGAATCAGAGCGGAAGCCTTGTAAATAGTGTTAAACTCTATGACAACATGGATGTC
TATATCCAAGGTCAGTGTTTCATTAGGGGAACTGATACCTCTATCTTTGATGAAATAAAA
CGACAACTAAAACCTTATATTCTAGGTTTGCTCCAAGGGCGTACAATGGTACGAAGTGCC
AATCTACGTGAAAAAGCTTCAATTGGTGATATAATAACAGGGGATAAAATAGACTATTGG
GCTTATCCTTCAGAAAACGGCAGTGGTTATATATCAGCTAGTGCTACTCAAGAACACACA
ATGGCAGTTAGTGCAGAAGACGCACGTAAAGATGGAGGATTATGGGTATAACTAGAAGT
TATTACTACACAGGGTATTGGTTACAAGAAGTTATTAATTTTGATGACTAA

Fig. 7

SENSITIVE AND RAPID METHOD FOR *CANDIDATUS LIBERIBACTER* SPECIES DETECTION

This patent application is a divisional patent application of and claims priority to U.S. patent application Ser. No. 13/564,957 filed on Aug. 2, 2012 which claims priority to U.S. Patent Application 61/514,315 filed Aug. 2, 2011.

BACKGROUND OF THE INVENTION

Field of the Invention

This invention relates DNA amplification methods including improved real-time PCR detection methods, for the detection of *Candidatus Liberibacter* species from citrus and psyllid hosts. It also relates to novel DNA sequences, novel primers and probes made from the novel DNA sequences, and to kits containing said primers and reagents for the DNA amplification methods for the detection of *Candidatus Liberibacter* species.

Description of the Related Art

Citrus huanglongbing (HLB), also known as citrus greening, is a destructive disease that was first noted in the early $20^{th}$ century in China (Zhao, Proc. Intl. Soc. Citriculture I: 466-469, 1981). This disease has spread throughout the global citrus producing regions, and has recently invaded North America, with first detection in Florida in 2005 (Knighten et al., USDA Departmental Release, Sep. 2, 2005). Three fastidious α-proteobacteria species of *Candidatus Liberabacter*, Ca. L. *asiaticus*, Ca. L. *americanus*, and Ca. L. *africanus* (Bove, J. Plant Pathology, Volume 88, 7-37, 2006; Gottwald et al, Plant Health Progr. Published online 2007) are associated with HLB. These bacteria have been shown to reside within sieve tube cells of infected plants (Tatineni et al., Phytopathology, Volume 98, 592-599, 2008) and to be vectored by psyllids, *Diaphorina citri* (Halbert and Manjunath, Fla. Entomologist, Volume 87, 330-353, 2004) and *Trioza erytreae* (Bove et al, 2006 supra; McClean and Oberholzer, S. Afr. J. Agri. Sci, Volume 8, 297-298, 1965; McClean, Phytophylactica, Volume 6, 45-54, 1974).

Although HLB presents systemically, low titer and uneven distribution of the HLB bacteria within infected plants (Tatineni et al, 2008, supra; Teixeira et al., Mol. Cell. Probes, Volume 22, 139-150, 2008; Li et al., Phytopathology, Volume 99, 139-144, 2009) can make reliable detection difficult. As such, many methods have been developed including biological indexing using graft and dodder transmission (Gottwald et al., 2007, supra), light or electronmicroscopy (Bove, 2006, supra), loop-mediated isothermal amplification (Okuda et al, Plant Disease, Volume 89, 705-711, 2005), polymerase chain reaction (PCR) (Jagoueix et al., Mol. Cell. Probes, Volume 10, 43-50, 1996; Hung et al, J. Phytopathology, Volume 147, 599-604, 1999; Tian et al., Proc. Conf. Int. Org. Cirus Virol., Volume 13, 252-257, 1996), and real-time PCR (Teixeria et al., Mol. Cell. Probes, Volume 22, 139-150, 2008; Li et al., Phytopathology, Volume 99, 139-144, 2009; Li et al., Plant Disease, Volume 92, 854-861, 2008; Li et al., Plant Diesease, Volume 91, 51-58, 2007; Li et al., J. Microbiol. Methods, Volume 66, 104-115, 2006; Wang et al., Plant Pathology, Volume 55, 630-638, 2006) to detect these Ca. *Liberibacter* bacteria. However, these detection methods are typically diagnostic only after HLB associated phenotypic symptoms are observable. Furthermore, the etiology of HLB remains, to a large extent, undefined.

Currently real-time PCR has become the preferred detection method of *Liberibacter* species (Teixeira et al., 2008, supra; Li et al., 2009, supra; Li et al., 2008, supra; Li et al., 2007, supra; Li et al., 2006, supra; Wang et al., 2006, supra). Relative to conventional PCR, real-time PCR offers both sensitive and rapid detection of these bacteria. Real-time PCR is reported to increase the sensitivity for *Liberibacter* detection by 10 times relative to nested PCR (Teixeira et al, 2008, supra) and 100 to 1,000 times relative to conventional PCR (Teixeira et al, 2008, supra; Wang et al., 2006, supra) for these bacteria. These real-time PCR methods target genes with low copy number; three copy 16S rDNA (Li et al., 2006 supra), single copy β-operon (Teixeira et al, 2008, supra) or single copy elongation factor Ts (EF-Ts) (Lin et al., J. Microbiol. Methods, Volume 81, 17-25, 2010). The reported real-time PCR low threshold limits are approximately ten gene copies for 16S rDNA and β-operon methods (Teixeira et al, 2008, supra; Li et al., 2008, supra), with elongation factor Ts (single closed tube dual primer) reporting single gene copy detectability (Lin et al, 2010, supra). However, current PCR detection methods can miss the targeted DNA for amplification because the Ca. *Liberibacter* bacteria can exist at extremely low titer in their host plant and insect.

While various methods for detecting Ca. *Liberibacter* species have been developed, there remains a need in the art for a method for detecting extremely low titer levels of Ca. *Liberibacter* species. The present invention described below includes a sensitive and rapid new method for detecting Ca. *Liberibacter* species as well novel DNA sequences; and primers and probes made from these novel sequences which are different from related art methods and primers.

SUMMARY OF THE INVENTION

It is therefore an object of the present invention to provide novel sequences having SEQ ID NO 25 and SEQ ID NO.: 30 from the genome of *Candidatus Liberibacter asiaticus* and to provide novel primers designed from SEQ ID NO.: 25 to detect the presence of *Candidatus Liberibacter* species in plants and insect hosts using DNA amplification methods.

Another object of the present invention is to provide a sensitive and rapid real-time PCR method wherein the method uses a primer having SEQ ID NO.: 1.

A still further object of the present invention is to provide a sensitive and rapid real-time PCR method wherein the method uses a primer having SEQ ID NO.: 2.

Another object of the present invention is to provide a sensitive and rapid real-time PCR method wherein the method uses a probe having SEQ ID NO.: 3.

A still further object of the present invention is to provide a sensitive and rapid real-time PCR method wherein the nucleic acid is obtain using a step of boiling the nucleic acid containing sample.

Another object of the present invention is to provide a sensitive and rapid real-time PCR method wherein the method uses a detector molecule.

A still further object of the present invention is to provide a sensitive and rapid real-time PCR method with a detector molecule wherein said detector molecule is a fluorescent reporter dye.

A still further object of the present invention is to provide a sensitive and rapid real-time PCR method with a probe wherein said probe has a detector molecule on one end and a quencher dye on the other end of said probe.

Another object of the present invention is to provide a kit for detecting *Candidatus Liberibacter* species in a plant or insect host wherein said kit comprises at least one primer having SEQ ID NO.: 1.

A still further object of the present invention is to provide a kit for detecting *Candidatus Liberibacter* species in a plant or insect host wherein said kit comprises at least one primer having SEQ ID NO.: 2.

Another object of the present invention is to provide a kit for detecting *Candidatus Liberibacter* species in a plant or insect host wherein said kit comprises at least one primer having SEQ ID NO.: 1, at least one primer having SEQ ID NO.: 2, and a probe having a detector molecule at one end and a quencher molecule at the other end.

A still further object of the present invention is to provide novel primers for use in a method for detecting *Candidatus Liberibacter* species wherein the primers have a SEQ ID NO.: 1 and SEQ ID NO.: 2.

A still further object of the present invention is to provide a novel probe for use in a method for detecting *Candidatus Liberibacter* species wherein said probe is a probe having SEQ ID NO.: 3.

Further objects and advantages of the present invention will become apparent from the following description.

BRIEF DESCRIPTION OF THE DRAWINGS

FIGS. 2 A-D are graphs showing representative dilution, melt and efficiency curves for LJ900fr by Quanta Biosciences Perfecta™ SYBR® Green FastMix™ master-mix on an ABI 7500 Fast real-time PCR machine, respectively.

FIG. 5 shows the pLJ153.1 hyvI gene sequence (single repeat), S1164 bases excerpt-SEQ ID NO.: 24.

FIG. 6 shows pLJ108.1 hyvI gene sequence (Full repeat), 2760 bases (excerpt)-SEQ ID NO.: 25.

FIG. 7 shows pLJ396.2 hyvII gene sequence (2 full and 4 partial repeat), 1371 bases (excerpt)-SEQ ID NO.: 30.

DETAILED DESCRIPTION OF THE INVENTION

The present invention includes novel DNA sequences SEQ ID NO.:25 and SEQ ID NO.:30 from the genome of Ca. *Liberibacter asiaticus*, primers designed from the novel DNA sequence, to methods of DNA amplification using the novel primers and to sensitive, rapid, cost effective methods for detecting the presence of the citrus Huanglongbing (HLB) associated bacteria from host plant and insect vectors. It provides methods to test for the presence of Ca. *Liberibacter* species using DNA amplification methods including quantitative real-time polymerase chain reaction (qPCR). Novel primers for use in DNA amplification methods include, for example, sensitive primers, LJ900 series (Table 1 below), designed against the multi-repeat region, up to approximately 12 repeats, within two unique genes of Ca. *Liberibacter* species relative to the current 16S rDNA based identification procedure.

Figures 1A, 1B:
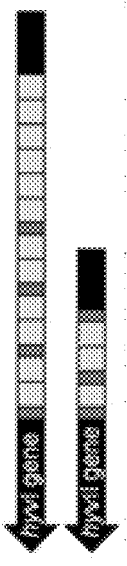
FIG. 1A is a schematic drawing showing hyvI and hyvII gene repeat sequence schematic with light and dark grey boxed representing full and partial repeat sequences, respectively. The arrow direction indicates gene orientation.
FIG. 1B shows the 100 base pair (bp) double stranded amplicon sequence of the LJ900f and LJ900r primers as bolded sequenced respectively.

Isolation of DNA for *Liberibacter* detection involved highly labor-intensive and lengthy purification protocols via either commercially available DNA isolation kits or traditional DNA extraction methodologies e.g. phenol. Compounding the difficulty for *Liberibacter* detection is its uneven distribution of bacteria within the host plants. Two prophage regions of the Ca. L *asiaticus* Psy2 genome were found that contained a large number of phage-related genes (Duan et al., Mol. Plant. Mcirobe. Interac., Volume 22, 1011-1020, 2009; Zhang et al., Mol. Plant. Microbe. Interact., Volume 24, 458-468, 2011). Based on cloning and sequencing of a 351 bp DNA fragment (cloning ID pLJ108) from one of the prophage regions, one gene containing multiple nearly identical tandem repeats (NITRs) was identified and named hyvI. The hyvI gene is approximately 2,760 bp long (SEQ ID NO.: 25) and putatively encodes a 919 amino acid acidic protein that has a pI of approximately 4.54 with a molecular weight of approximately 103.5 kDa. Using Tandem repeats Finder (Benson, Nucleic Acids Res., Volume 27, 573-580, 1999) and manual arrangements; the intragenic tandem repeat region was identified in the hyvI gene. This region includes approximately 12 full NITRs and approximately 4 partial tandem repeats. Each full repeat is of approximately 132 bp, with three partial repeats of approximately 48 bp sitting between full repeats 6 and 7, 8 and 9, and 10 and 11. There is an additional approximately 33 bp repeat at the 3' end of the entire tandem repeat region (FIG. 1). The partial repeat sequences are nearly identical to the first 48 or 33 bp of the 132 bp-full repeat. The similarity among 12 full repeats within the hyvI gene was approximately 93-100% at the nucleic acid level (FIG. 1) and approximately 82-100% at the putative protein level (FIG. 2). Based on the hyvI gene sequence, the hyvII gene (SEQ ID NO.: 30) was identified from another prophage region-Psy62-FP2:38, 551 bp; Accession number JF773396 of the Ca. L *asiaticus* Psy62 genome. The hyvII gene is an approximately 1,026 bp and putatively encodes an approximately 341 amino acid acidic protein with having a pI of approximately 5.1 and a molecular weight of approximately 38.9 kDa. In Ca. L. *asiaticus* Psy 62 genome, hyvII only contained one partial repeat unit and shared approximately 92% identity with hyvI on downstream (outside) 3' end of the repeat unit. However, based on hyvII gene sequencing cloned from global orgin isolates including different host of Ca. L *asiaticus* in Florida, the repeat number in hyvII gene can be up to 2 full, 4 partial in Florida isolate (FIG. 1) or 3 full, 3 partial repeats in Thailand isolates.

The recent sequencing of the Ca. L. *asiaticus* genome by the inventors using a metagenomics approach (Duan et al., Mol. Plant. Microbe. Interact., Volume 22, 1011-1020, 2009), has revealed two unique hypothetical genes located within a prophage region of the genome that are designated as hyvI (YP_003084345.1[and hyvII (HQ263713). These genes contain multiple nearly identical tandem-repeat sequences of approximately 132 base pairs (bp) for each full-length repeat (Zhou et al., Appl. Environ., Microbiol, available on line Jul. 22, 2011).

As real-time PCR allows amplification and detection of shorter target sequences, the approximately 100 bp core sequence of each repeat (FIG. 1) provides ideal targets for development of sensitive real-time PCR methods using both SYBR Green 1 (LJ900fr) and TaqMan® (LJ900fpr) chemistries. As hyvI/hyvII may contain up to a combined fifteen nearly identical repeats (FIG. 1), targeting these repeats provides a significantly increased probability for Ca. L asiaticus detection in both plant and insect hosts. The present invention uses the nearly identical approximately 132 bp tandem-repeats of two Ca. L. asiaticus prophage genes for real-time PCR. The invention improves the detection sensitivity and reliability of Ca. L. asiaticus using either SYBR Green 1 (LJ900fr) or TaqMan® (LJ900fpr) compared with prior art real-time PCR methods.

Real-time polymerase chain reaction (PCR) is an existing research technique that utilizes specifically engineered DNA sequences (two primers and a fluorescently labeled probe for TaqMan based detection or SYBR Green 1 for intercalation dye detection) to detect and quantify target sequences of DNA. The probe contains a fluorescent reporter dye on one end and a quencher dye on the other (Table 1). For TaqMan detection during each amplification cycle the probe (SEQ ID NO.: 3) attaches along with the primers (SEQ ID NO 1 and SEQ ID NO 2) to the target sequence of DNA to be copied. As the DNA strand is copied, the reporter dye is released from the probe sequence and then emits a fluorescent signal. The amount of fluorescence increases with each PCR cycle in proportion to the amount of target DNA amplified. This results in direct detection and quantification of the target DNA sequence with a high degree of specificity (no false positives), accuracy, and sensitivity.

Sets of DNA primers and DNA probes that are specific for Ca. L. species were developed for molecular detection and semi-quantification of Ca. L. species with DNA amplification methods including real-time PCR technology (Table 1). One of ordinary skill in the art, given the detailed description of the present invention can make any primer for use in DNA amplification methods using DNA sequences for SEQ ID NO.: 25 and SEQ ID NO.: 30. The present invention includes any primer made from DNA sequences SEQ ID NO.: 25 and SEQ ID NO.: 30 that is specific for detecting Ca. L. species in plants and insect hosts. Specificity of the primers and probes can be and was assessed using non-infected citrus and psyllid populations as well as citrus infected with Ca. L. asiaticus (Tables 2 and 3). The sensitivity of this assay was determined to be able to detect single copy levels of hyvI or hyvII within a given sample.

The invention can be used to identify trees or insects that are contaminated with Ca. L. species. The ability to readily identify an organism infected with or carrying Ca. L. species will allow for treatment regimens and disease management strategies implemented in emerging disease areas and can be used for highly sensitive site monitoring of disease progression.

In the present invention the DNA amplification methods are coupled with a modified boil DNA isolation (De Barro et al., Austral. J. Entomol., Volume 36, 149-152, 1997, herein incorporated by reference in its entirety) that significantly reduces the DNA harvest cost associated with typical high throughput sample processing. Below is the method for the boil DNA isolation:

Make 50 mL "Cell Lysis/DNA Isolation Buffer":
    Add: 2.5 mL of 1 M KCl
    2.5 mL of 1 M Tris buffer at pH 8.4
    225 µL of Tween 20
    225 µL of NP-40
    ddH$_2$O up to 50 mL total volume (~44.55 mL)
    Filter Sterilize 0.2 µm filter into a sterile container and store at room temperature Processing Step by Step as Follows:
1. Obtain plant sample (~0.01 g or less is all that is required from such a sample we have detected positive samples out to $10^{-7}$ dilutions by this method)
2. Place plant sample into sterilized 2 mL tubes containing (sterile) steel shot/shards and add 100 µL filter sterile "cell lysis/DNA isolation buffer"
3. Disrupt/homogenize tissue to break up plant material
4. Pipette off 90-100 µL of buffer (do not worry about carry-over plant materials at this stage) and transfer into a sterile PCR tube and close the cap
5. Place PCR tube into PCR thermal cycler and incubate at 95 degrees C. for 5 minutes (lid at 105 degrees C.)
6. After PCR incubation place tube onto ice for 5 minutes
7. Transfer buffer from centrifuge tube to an alternate sterile micro-centrifuge tube and centrifuge at max speed for 1 min (or until all plant materials are pelleted)
8. Pull off supernatant and put into a sterile labeled tube
9. The sample is now ready for use with the LJ900 Series qPCR reactions or for long term storage at −80 degrees C.

NOTE: This method is not compatible with TaqMan qPCR reactions and only works with SYBR Green 1 (intercalation dye) qPCR methods. Also a 95 degrees C. water bath may substitute for the PCR thermal cycler herein the described boil method.

Samples are obtained from material to be tested, for example a citrus tree or psyllid, and is then processed to extract polynucleotide's from the sample, particularly polynucleotide's from target organisms that may be present in the material After extraction and processing according to methods described herein or otherwise known in the art, the sample is treated with reagents that comprise the primer SEQ ID NO.: 1, primer SEQ ID NO.: 2, or SEQ ID NO.: 1, SEQ ID NO.: 2, and SEQ ID NO.: 3, sample DNA and either Perfect SYBR Fastmix or TaqMan. The sample is then processed according to real-time PCR amplification methods. The product is first amplified using the primers. Binding of a labeled probe to a target sequence within the PCR product that corresponds with a target region in the genomic DNA of the contaminating microorganism, Ca. L. species, signals the presence of the Ca. L. species.

Therefore, the combination of the unique primers with a modified boil DNA extraction method and real-time PCR technology ensured specific and sensitive detection of the presence of Ca. L. species.

Statistical significances between comparative methods (LJ900, HLBaspr, STDP, etc.) were evaluated using single factor ANOVA at 95% (P=0.05) confidence interval with MS Excel 2007 (Microsoft, Redmond, Wash.), comparative data set values where P<0.05 were considered statistically significant.

The following examples are intended only to further illustrate the invention and are not intended to limit the scope of the invention as defined by the claims.

EXAMPLE 1

The hyvI and hyvII genes were identified by analyzing the PCR amplicons form psyllid 62 which was the genomic DNA source used to produce the Ca. L. *asiaticus* genomic sequence, was generated during the gap closing process of the Ca. L. *asiaticus* genome sequence study (Duan et al., Mol. Plant. Microb Interact., 2009, supra, herein incorporated by reference in its entirety) and verified using BAC clones of Ca. L. *asiaticus* genome. Partial hyvI amplicons were subsequently cloned into the pCR® 2.1-TOPO® cloning vector in accordance with manufacture protocol (Invitrogen, Carlsbad, Calif.) and sequenced. Clone LH153.1 was shown to contain a single repeat of a complete 132 bp segment.

New primers LJ900f (forward), LJ900r (reverse) and LJ900p TaqMan® probe (Table 1), were designed based on the tandem-repeats of hyvI/hyvII using OLIGO 7 Primer Analysis Software version 7.23 (Molecular Biology Insights, Cascade, Colo.) targeting an integral 100 bp core sequence of the approximately 132 bp repeat (FIG. 1). Table 1 TaqMan® probes were labeled 5' with either 6-carboxy-fluorescein (6-FAMT™) or tetrachloro-6-carboxy-fluorescein (TET) reporters and 3' with Iowa Black FQ or Black Hole Quencher (BHQ-2) quenchers. Integrated DNA technologies (IDT, Coralville, Iowa) synthesized all primers and probes used in this study (Table 1).

TABLE 1

PCR and real-time PCR primers

| Sequence (5' → 3') | Purpose |
|---|---|
| GCCGTTTTAACACAAAAGATGAATATC LJ900f SEQ ID NO.: 1 | LJ900fr repeat sequence real-time PCR |
| ATAAATCAATTTGTTCTAGTTTACGAC LJ900r SEQ ID NO.: 2 | |
| [a]ACATCTTTCGTTTGAGTAGCTAGATCATTGA[b] LJ900p SEQ ID NO.: 3 | LJ900fpr TaqMan ® real-time PCR probe |
| CGGTGAATGTATTAAGCTGAGGCGTTCC SEQ ID NO.: 4 | STDP (nested) real-time PCR |
| ACCCACAACAAAATGAGATACACCAACAACTTC SEQ ID NO.: 5 | |
| CGATTGGTGTTCTTGTAGCG SEQ ID NO.: 6 | |
| AACAATAGAAGGATCAAGCATCT SEQ ID NO.: 7 | |
| [a]AATCACCGAAGGAGAAGCCAGCATTACA[b] SEQ ID NO.: 8 | |
| TCGAGCGCGTATGCAATACG SEQ ID NO.: 9 | HLBaspr real-time PCR |
| GCGTTATCCCGTAGAAAAAGGTAG SEQ ID NO.: 10 | |
| [a]AGACGGGTGAGTAACGCG[b] SEQ ID NO.: 11 | |
| CGAGCGCGTATTTATACGAGCG SEQ ID NO.: 12 | HLBafpr real-time PCR[e] |
| GAGCGAGTACGCAAGTACTAG SEQ ID NO.: 13 | HLBampr real-time PCR[e] |
| GTATGCCACGTCGCATTCCAGA SEQ ID NO.: 14 | COXfpr (multiplex) real-time PCR |
| GAATGCCCTTAGCAGTTTTGGC SEQ ID NO.: 15 | |
| [c]ATCCAGATGCCTACGCTGG[d] SEQ ID NO.: 16 | |
| ACTCCTACGGGAGGCAGCAG SEQ ID NO.: 17 | Universal Eubacterial 16S real-time PCR |
| ATTACCGCGGCTGCTGG SEQ ID NO.: 18 | |
| TCTACGRATTTCACCYCTAC SEQ ID NO.: 19 | Universal α-proteobacteria real-time PCR[f] |
| GGACAAGGGGATATTGGATAATGATG SEQ ID NO.: 20 | 'Ca. *L. americanus*' β operon real-time PCR |

TABLE 1-continued

PCR and real-time PCR primers

| Sequence (5' → 3') | Purpose |
|---|---|
| ATTAAGAGTTCTAAGCAACCTGACAG<br>SEQ ID NO.: 21 | |
| CGCCCGTTTCCGTTGT<br>SEQ ID NO.: 22 | SYBR ® Green real-time PCR of 'Ca. L. asiaticus' β operon |
| AGCCTCTTTAAGCCCTAAATCAG<br>SEQ ID NO.: 23 | | f = Forward, r = Reverse, p = TaqMan ® Probe
[a]6-FAM ™,
[b]Iowa Black FQ,
[c]TET,
[d]BlIQ-2
[e]Use with common probe (HLBp) and reverse primer (HLBr)
[f]ALF685f is used in combination with EUB518r universal 16S reverse primer

EXAMPLE 2

A series of in silico evaluations of both LJ900f and LJ900r primers and LJ900p probe were done using the NCBI BLAST megablast algorithm parameters for highly similar sequence alignment against the nucleotide (nr/nt) database having either the Ca. L. asiaticus genome that either included or excluded in separate searches respectively for each. Additional specificity of these primers and probe was evaluated by real-time PCT against a variety of DNA extracts from plant pathogens, Xanthomonas citri subsp. citri, X. axonopodis pv. citrumelo, Ralstonia solanacearum, Escherichia coli DH5α, soil bacteria in USHRL (United State Horticulture Research Laboratory) Picos farm and the USHRL facility greenhouse maintained citrus varieties and from plants of proximal and distal locations indicating specificity for the LJ900 primers (f, r, p) to Ca. L. species bacteria.

The specificity of the LJ900 primers and probe was evaluated in real-time PCR reactions, as stated above, that returned no detectable cycle threshold values (data not shown). Also included within Table 2 are non-detectable hyvI/hyvII sample numbers 5, 10, 14, 22 (citrus varieties) and 30 (psyllid D. citri), each representative of a larger group of USHRL maintained citrus and psyllid populations having non-detectable Ct values by LJ900 testing (data not shown). Additionally, multiple LJ900 primer amplicon products from various Ca. L. asiaticus hosts were cloned and sequenced. These data indicate primer fidelity to the hyvI/hyvII target as each sequence from the clone libraries returned only target specific amplification of the repeated sequence (data not shown). In addition to these, greater than about one-hundred putative HLB negative DNA samples of multiple citrus varieties received as isolated DNA's form the USDA National Clonal Germplasm Repository for Citrus and Dates (Riverside, Calif.) indicated no detectable Ct values for all replicate samples, real-time PCR of total universal Eubacterial 16S rDNA and α-Proteobacteria populations was conducted, indicating average total 16S rDNA Ct values in the low to mid-teens with low thirty values for α-Proteobacteria analyses (data not shown). Table 3 DNA sample #29 (CA Rep. #67) represents these collective California LJ900 negative samples. All combined these data indicate specificity for hyvI/hyvII for LJ900 methods to specifically detect Ca. L. species bacteria.

TABLE 2

Detection of 'hyvI/hyvII' repeat by LJ900fr from citrus seedlings or seedling fed psyllids

| | | | LJ900fr | |
|---|---|---|---|---|
| Host | Sample # | Name | Ct value | Tm degrees C. |
| Pomelo | 1 | Pomelo G7 | 23.88 | 74.86 |
| Pomelo | 2 | Pomelo H3 | 25.31 | 74.33 |
| Pomelo | 3 | Pomelo H5 | 34.38 | 73.97 |
| Pomelo | 4 | Pomelo E5 | 34.39 | 75.40 |
| Pomelo | 5 | Pomelo F6 | ND | 63.43 |
| Trifoliate | 6 | TF-#33 | 30.41 | 74.65 |
| Trifoliate | 7 | TF-#31 | 31.22 | 74.65 |
| Trifoliate | 8 | TF-#25 | 35.52 | 75.00 |
| Trifoliate | 9 | TF-#32 | 36.48 | 75.35 |
| Trifoliate | 10 | TF-#37 | ND | 63.41 |
| Grapefruit | 11 | I-GF-Anti 07.31.09 #13 | 27.96 | 74.16 |
| Grapefruit | 12 | I-GF-H₂0 07.20.09 #3 | 28.94 | 74.33 |
| Grapefruit | 13 | I-GF-Anti 07.31.09 #8 | 36.46 | 75.04 |
| Grapefruit | 14 | I-GF-Anti 07.31.09 #28 | ND | 63.41 |
| Sweet Orange | 15 | I-SO-Anti 01.21.10 #17 | 29.47 | 74.51 |
| Sweet Orange | 16 | 1-SO-H₂O 01.21.10 #14 | 30.39 | 74.15 |
| Sweet Orange | 17 | I-SO-H₂O 07.10.09 #10 | 30.60 | 75.02 |
| Sweet Orange | 18 | I-SO-Anti 07.14.09 #10 | 31.27 | 74.11 |
| Sweet Orange | 19 | I-SO-H₂O 07.10.09 #8 | 31.40 | 75.21 |
| Sweet Orange | 20 | I-SO-Anti 07.14.09 #3 | 35.54 | 75.21 |
| Sweet Orange | 21 | I-SO-Anti 07.14.09 #16 | 36.80 | 75.21 |
| Sweet Orange | 22 | I-SO-Anti 01.21.10 #14 | ND | 63.61 |
| Seedling fed psyllid (D. citri) | 23 | #22 14-6-11-5 | 28.29 | 74.80 |
| Seedling fed psyllid (D. citri) | 24 | #23 14-6-11-5 | 30.86 | 74.99 |
| Seedling fed psyllid (D. citri) | 25 | #34 14-6-11-5 | 31.82 | 75.35 |
| Seedling fed psyllid (D. citri) | 26 | #21 14-6-11-5 | 34.17 | 75.44 |
| Seedling fed psyllid (D. citri) | 27 | #31 14-6-11-5 | 34.62 | 75.35 |
| Seedling fed psyllid (D. citri) | 28 | #14 14-6-11-5 | 34.84 | 74.80 |
| Seedling fed psyllid (D. citri) | 29 | #3 14-6-11-5 | 35.35 | 74.62 |
| Seedling fed psyllid (D. citri) | 30 | #4 14-6-11-5 | ND | 63.46 |

ND = No Detection

TABLE 3

Real-time PCR data comparison of hyvI/hyvII detection by LJ900fr, LJ900fpr, and HLBaspr

| | Sample | | Mean Ct value by Method (±St. dev. Mean Ct) | | | ΔCt | | |
|---|---|---|---|---|---|---|---|---|
| Citrus Host | # | Name | LJ900fr | LJ900fpr | HLBaspr | LJ900fr − HLBaspr | LJ900fpr − HLBaspr | LJ900fpr − LJ900fr |
| Blood Orange | 1 | R2T6 | $18.70^{(\pm 0.16)}$ | $26.30^{(\pm 1.81)}$ | $29.89^{(\pm 0.15)}$ | −11.19 | −3.59 | −7.60 |
| Trifoliate | 2 | 09-002 | $27.26^{(\pm 0.29)}$ | $32.76^{(\pm 4.71)}$ | ND | N/A | N/A | −5.50 |
| Sour Orange | 3 | R7T6 | $19.31^{(\pm 0.17)}$ | $26.29^{(\pm 0.18)}$ | $30.26^{(\pm 0.13)}$ | −10.95 | −3.97 | −6.98 |
| Sweet Orange | 4 | R3T7-G | $19.93^{(\pm 0.07)}$ | $26.86^{(\pm 0.45)}$ | $29.47^{(\pm 0.06)}$ | −9.54 | −2.61 | −6.93 |
| Sweet Orange | 5 | R3T7-Y | $15.01^{(\pm 0.31)}$ | $20.93^{(\pm 1.01)}$ | $22.90^{(\pm 0.02)}$ | −7.89 | −1.97 | −5.92 |
| Dancy Tangerine | 6 | R10T6 (N) | $11.20^{(\pm 1.02)}$ | $16.92^{(\pm 0.17)}$ | $22.61^{(\pm 0.06)}$ | −11.41 | −5.69 | −5.72 |
| Lemon | 7 | R11T11 | $12.76^{(\pm 0.21)}$ | $17.93^{(\pm 0.81)}$ | $23.16^{(\pm 0.14)}$ | −10.40 | −5.23 | −5.17 |
| Orangequat | 8 | R12T9 | $12.70^{(\pm 0.07)}$ | $18.50^{(\pm 1.31)}$ | $21.85^{(\pm 0.10)}$ | −9.15 | −3.35 | −5.80 |
| Pomelo | 9 | R8T1-GY | $19.44^{(\pm 0.20)}$ | $25.26^{(\pm 3.06)}$ | $29.58^{(\pm 0.06)}$ | −10.14 | −4.32 | −5.82 |
| Pomelo | 10 | R8T1-M | $14.52^{(\pm 0.16)}$ | $20.04^{(\pm 1.52)}$ | $24.80^{(\pm 0.12)}$ | −10.28 | −4.76 | −5.52 |
| Pomelo | 11 | R8T1-Y | $26.16^{(\pm 0.26)}$ | $32.45^{(\pm 0.30)}$ | $36.47^{(\pm 0.55)}$ | −10.31 | −4.02 | −6.29 |
| Pomelo | 12 | R8T4-Y | $12.90^{(\pm 0.35)}$ | $18.87^{(\pm 1.29)}$ | $21.89^{(\pm 0.07)}$ | −8.99 | −3.02 | −5.97 |
| Pomelo | 13 | R8T4-M | $18.16^{(\pm 0.19)}$ | $25.83^{(\pm 1.67)}$ | $27.80^{(\pm 0.10)}$ | −9.64 | −1.97 | −7.67 |
| Pomelo | 14 | R8T1-11 | $27.43^{(\pm 0.24)}$ | $35.50^a$ | $37.99^{(\pm 0.82)}$ | −10.56 | −2.49 | −8.07 |
| Pomelo | 15 | R8T1-14 | $30.48^{(\pm 1.67)}$ | $35.56^{(\pm 0.41)}$ | ND | N/A | N/A | −5.08 |
| Pomelo | 16 | R8T1-15 | $28.78^{(\pm 0.33)}$ | $34.08^{(\pm 0.71)}$ | ND | N/A | N/A | −5.30 |
| Pomelo | 17 | R8T1-31 | $26.82^{(\pm 0.21)}$ | $34.80^{(\pm 1.38)}$ | ND | N/A | N/A | −7.98 |
| Pomelo | 18 | R8T1-72 | $26.60^{(\pm 0.29)}$ | $33.04^{(\pm 0.71)}$ | ND | N/A | N/A | −6.44 |
| Pomelo | 19 | R8T1-129 | $27.39^{(\pm 0.76)}$ | $34.27^{(\pm 0.93)}$ | ND | N/A | N/A | −6.88 |
| Pomelo | 20 | R8T1-130 | $24.89^{(\pm 0.11)}$ | $30.20^{(\pm 0.30)}$ | ND | N/A | N/A | −5.31 |
| Melogold hybrid | 21 | R8T3-M | $15.84^{(\pm 0.87)}$ | $21.03^{(\pm 0.70)}$ | $24.93^{(\pm 0.17)}$ | −9.09 | −3.90 | −5.19 |
| Melogold hybrid | 22 | R8T3-Y | $15.03^{(\pm 0.43)}$ | $18.99^{(\pm 0.20)}$ | $23.15^{(\pm 0.14)}$ | −8.12 | −4.16 | −3.96 |
| Melogold hybrid | 23 | R8T3-4 | $27.58^{(\pm 0.12)}$ | $35.07^{(\pm 0.92)}$ | ND | N/A | N/A | −7.49 |
| Melogold hybrid | 24 | R8T3-12 | $28.05^{(\pm 0.31)}$ | $34.81^a$ | ND | N/A | N/A | −6.76 |
| Melogold hybrid | 25 | R8T3-13 | $26.58^{(\pm 0.24)}$ | $33.47^{(\pm 0.31)}$ | ND | N/A | N/A | −6.89 |
| Melogold hybrid | 26 | R8T3-101 | $13.66^{(\pm 0.19)}$ | $18.85^{(\pm 0.74)}$ | $24.25^{(\pm 0.08)}$ | −10.59 | −5.40 | −5.19 |
| Melogold hybrid | 27 | R8T3-111 | $18.03^{(\pm 0.43)}$ | $25.08^a$ | $27.77^{(\pm 0.23)}$ | −9.74 | −2.69 | −7.05 |
| Melogold hybrid | 28 | R8T3-NT | $26.32^{(\pm 0.28)}$ | $33.47^{(\pm 0.23)}$ | ND | N/A | N/A | −7.15 |
| [b]CA Rep. Citrus | 29 | #67 | ND | ND | ND | N/A | N/A | N/A |
| | | Mean ΔCt→ | | | | $-9.88^{(\pm 1.00)}$ | −3.71 (±1.16) | $-6.27^{(\pm 1.04)}$ |

N/A = Not Applicable
ND = No Detection
[a]Insufficient DNA precluding technical replicates, no reportable St. Dev.
[b]CA Rep. Citrus (#67) = California Citrus Repository sample #67 is representative of >68 California Citrus repository samples tested, each being negative by these methods

EXAMPLE 3

Primer sets LJ900fr (with SYBR Green 1) and LJ900fpr (with TaqMan®) final optimal primer concentrations are approximately 600 and 900 nanomolar (nM) of LJ900f and LJ900r respectively, with an addition of approximately 500 nM of LJ900p to the LJ900fpr. These ratios were determined via gridded-paired primer concentrations against the single repeat pLJ153.1 (having a minimum of three technical replicates per pairing). The optimal annealing temperature is 62 degrees C. for maximum efficiency for both LJ900fr and LJ900frp methods as determined via gradient temperature experiments.

Amplification settings for LJ900fr are, initial denaturation (one cycle) at approximately 95 degrees C. for approximately 3 minutes, followed by approximately 40 cycles at approximately 95 degrees C. for approximately 3 seconds, then approximately 62 degrees C. for approximately 30 seconds, with fluorescence signal capture at the end of each 62 degree C. step followed by a default melt (disassociation) stage. For LJ900fr, amplification settings include, initial denaturation (one cycle) at approximately 95 degrees C. for approximately 30 seconds, with PCR cycling of approximately 40 cycles at approximately 95 degrees C. for approximately 3 seconds, then approximately 62 degrees C. for approximately 30 seconds and fluorescence signal capture at the end of each approximately 62 degree C. step. Reactions were run on the Applied Biosystems 7500 Fast real-time PCR system (Applied Biosystems (ABI), Foster City, Calif.). Cycle threshold (Ct) values were analyzed using ABI 7500 Software version 2.0.1 having a manually set threshold at approximately 0.1 with automated baseline settings used for all samples analyzed. Unless otherwise indicated, all DNA quantities for comparative samples by method were normalized at approximately 2 μl total per individual approximately 15 μl reaction.

Pursuant with the ABI tutorial document "Creating a Standard Curve with a Plasmid DNA Template" (ABI Support Tutorial, 2003) primer efficiency/standard curve evaluations of LJ900fr primers employed copy number standardized pLJ153.1 plasmid (n=approximately 202 bp total, insert approximately 271 bp) adjusted to $10^6$ copies/μl and serially diluted to single copy levels. The efficiency evaluations of LJ900fr were performed in triplicate (having approximately 3× replicates per decade dilution) from approximately $10^6$ to single copy in $H_2O$ and with background DNA at approximately 50 ng/15 μl reaction of background Ca. L. asiaticus negative citrus DNA (FIG. 2).

Primer efficiency was determined by tenfold serial dilutions form approximately $10^6$-1 copy per approximately 15 μl reaction of pLJ153.1 in water (FIG. 2A) with additional spiking of approximately 50 ng per reaction of total Ca. L. asiaticus-negative citrus DNA. Using the plasmid for template, in water the LJ900 primers had an efficiency of approximately 100.91% (Slope=approximately −3.300, $R^2$=approximately 0.999) (FIG. 2C) and with citrus background DNA present of approximately 100.59% (Slope=approximately −3.308, $R^2$=approximately 0.999) (FIG. 2D).

Li et al in 2008, demonstrated the addition of background DNA levels at approximately 50 ng/µl in serial dilutions of template DNA that altered the detection threshold for low level target detection (Li, 2008). As Ca. L asiaticus detection employs unknown levels of host background DNA relative to Ca. L. asiaticus target within each sample that may be in excess of those previously tested levels, previous experiments were extended to determine the potential deleterious effects on cycle threshold detection that elevated relative background DNA levels for LJ900 detection. To do this, the background DNAs were increased to approximately 100 and 200 ng/15 µl reaction with control Ca. L. asiaticus negative citrus DNA to which pLJ153.1 (single repeat containing plasmid) was serially diluted from approximately $10^6$ to 1 copy for each background DNA level. From these, increases of one and three Ct's at the approximately 100 and 200 ng/15 µl reaction levels were observed respectively, relative to baseline detection at approximately 0 and 50 ng/15 µl reaction value from which no significant difference between approximately 0 and 50 ng/15 µl reactions for LJ900 primer efficiency was observed (data not shown). Further expanding this to a limit of detection, elevated interfering background DNA was increased of pLJ153.1 concentrations from approximately $10^6$ to one copy at each background concentration of interfering DNA at approximately 200, 500, and 1,000 ng/15 µl respectively. Commercially available salmon sperm DNA was substituted in lieu of Ca. L. asiaticus DNA because of ease of obtaining larger amounts of genomic DNA for all experiments. Substitution of salmon sperm DNA at approximately 200 ng/15 µl (approximately 200:1 background to target ratio) reaction demonstrated equivalent results previously described with native citrus DNA (data not shown), indicating background DNA source was not a critical factor. For single copy numbers of pLJ153.1, analytical detectability at approximately 50% positive detection for all replicates (approximately 50% of replicate wells were positive/negative) at approximately 500 ng total DNA/15 µl (approximately 500:1, salmon sperm DNA:pLJ153.1) occurred at approximately 36 Ct's whereas approximately 1,000 ng/15 reactions (approximately 1,000:1) exceeded the limit of detection for LJ900fr (data not shown). For levels in excess of single copy pLJ153.1 at the approximately 1,000 ng/15 µl reaction background DNA, the hyvI/hyvII repeat target was detected in all replicates. The mean change (Δ) in Ct from approximately 50 to 1,000 ng/15 µl reaction background (salmon sperm) for all diluted pLJ153.1/15 µl reaction levels was approximately +5.65 Ct's having a standard deviation of the difference from the mean CT (St. dev.) of approximately ±0.79 with no significant difference (P>0.05, P=0.984) in ΔCt between the dilutions. This suggests that the effect of interfering background DNA levels resulted in a common shift in Ct for each dilution and was not pLJ153.1 quantity dependent.

EXAMPLE 4

All real-time PCR reactions were performed in Micro-Amp® Fast Optical 96 well reaction plates (ABI) with MicroAmp Optical Adhesive Film (ABI) plate coverings using the same 7500 Fast real-time PCR system (ABI) accordingly at approximately 15 µl total reaction volumes. For TaqMan® real-time PCR reactions with the LJ900fpr method and the 16S rDNA standard for Ca. L. asiaticus detection HLBaspr, HLBampr (americanus), HLBafpr (africanus), or COXfpr (plant cytochrome oxidase) methods (Li et al., 2006), each used the ABI TaqMan® Fast Universal PCR Master Mix (2×) No AmpErase® UNG (Applied Biosystems Inc, Foster City, Calif.). The EF-Ts gene targeting Single Tube Dual Primer TaqMan® real-time PCR (Lin et al., 2010) (STDP) method employed ABI TaqMan® Universal PCR Master Mix (2×) (ABI). In SYBR Green 1 (SGI) real-time PCR reactions with LJ900fr, β-operon methods rplJAm (americanus) and rplLAs (asiaticus) (Teixeira et al, 2008), or HLBasr/SG1 employed PerfeCTa™ SYBR® Green FastMix™ 2× master-mix (Quanta Biosciences, Inc., Gaithersburg, Md.) and for comparison Promega GoTaq® real-time PCR Master Mix (Promega) was used. Despite the established use of SG1 in real-time PCR (Zipper et al., Nucleic Acids Res., Volume 32, e103, 2004; Wittwer et al., Biotechniques, Volume 22, 176-181, 1997), concerns arise with respect to potential signal interference of SG1 bound non-targeted dsDNA species. As SG1 is nondiscriminatory, an analysis of potential background fluorescence with known Ca. L. asiaticus positive citrus host DNA (approximately 200 ng/reaction) was performed without (minus) LJ900 primers. Real-time observations indicated that within the first 1-3 cycles, apparent background fluorescence detection occurred, and was maintained stably throughout the course of the run; however, upon completion these were normalized to zero (observed observations) forming the baseline fluorescence for the samples.

Figure 2A:
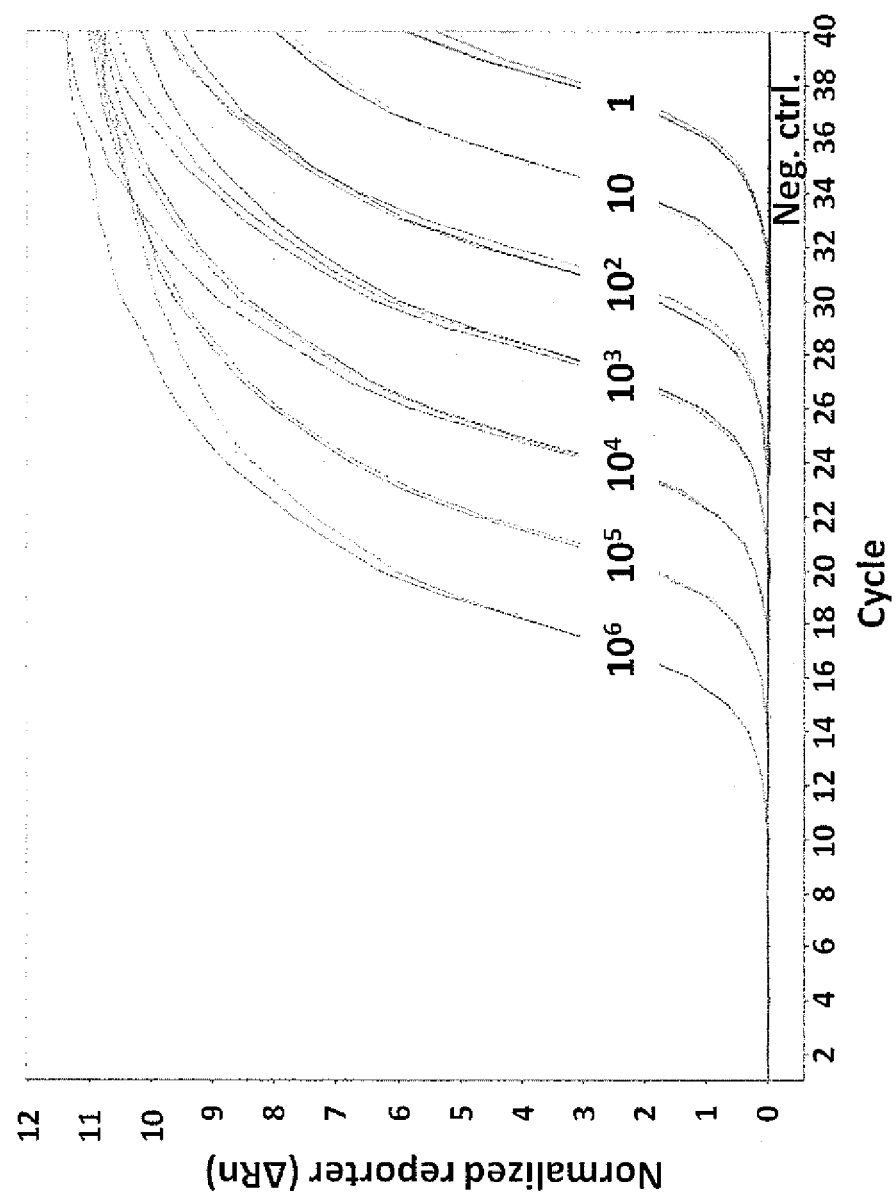
FIG. 2A is a serial dilution of the pLJ153.1 (single repeat containing plasmid) in water ranging from approximately $10^6$ to 1 repeat copy tested by LJ900fr indication detection at each dilution.
Figure 2B:
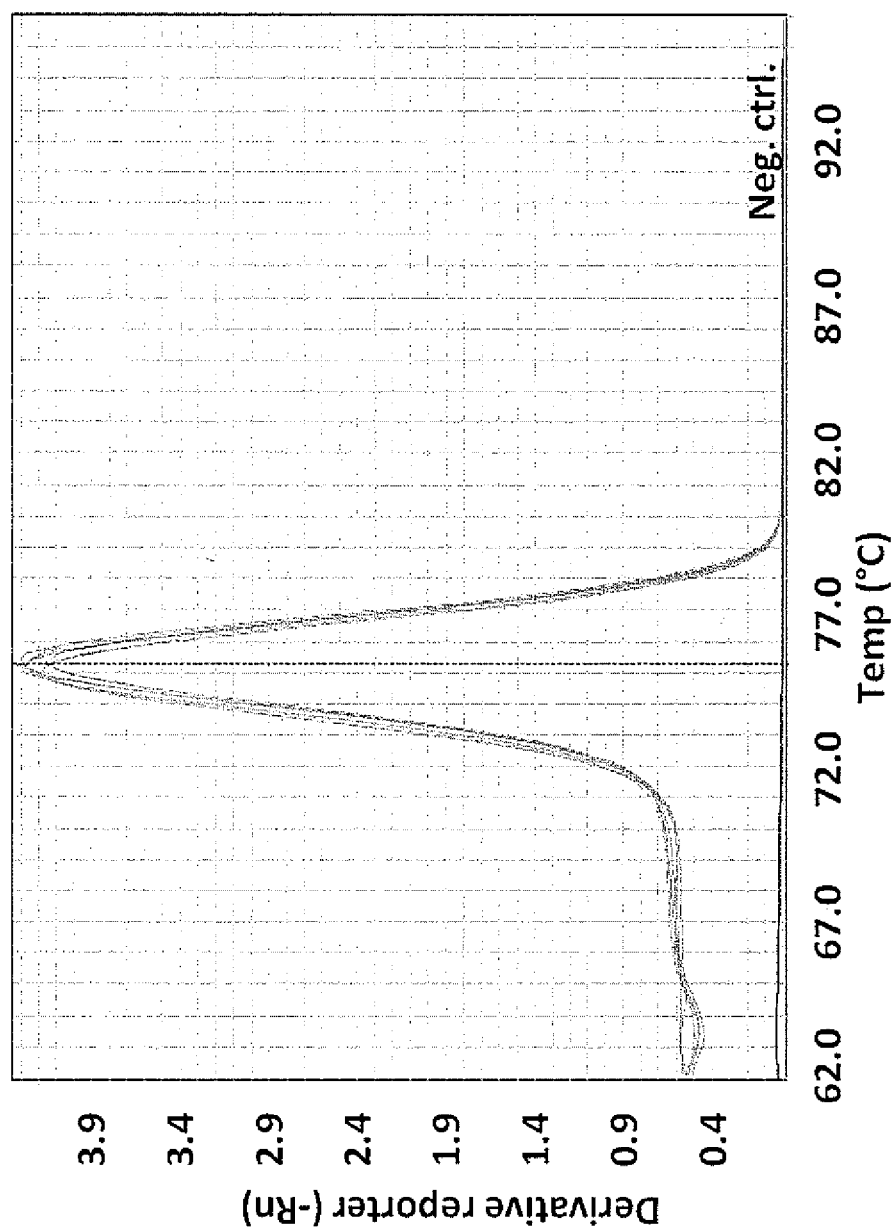
FIG. 2B is a melt curve of LJ900fr indicating a characteristic melt profile obtained on the ABI 7500 Fast real-time PCR machine with SYBR Green 1.
Figure 2C:
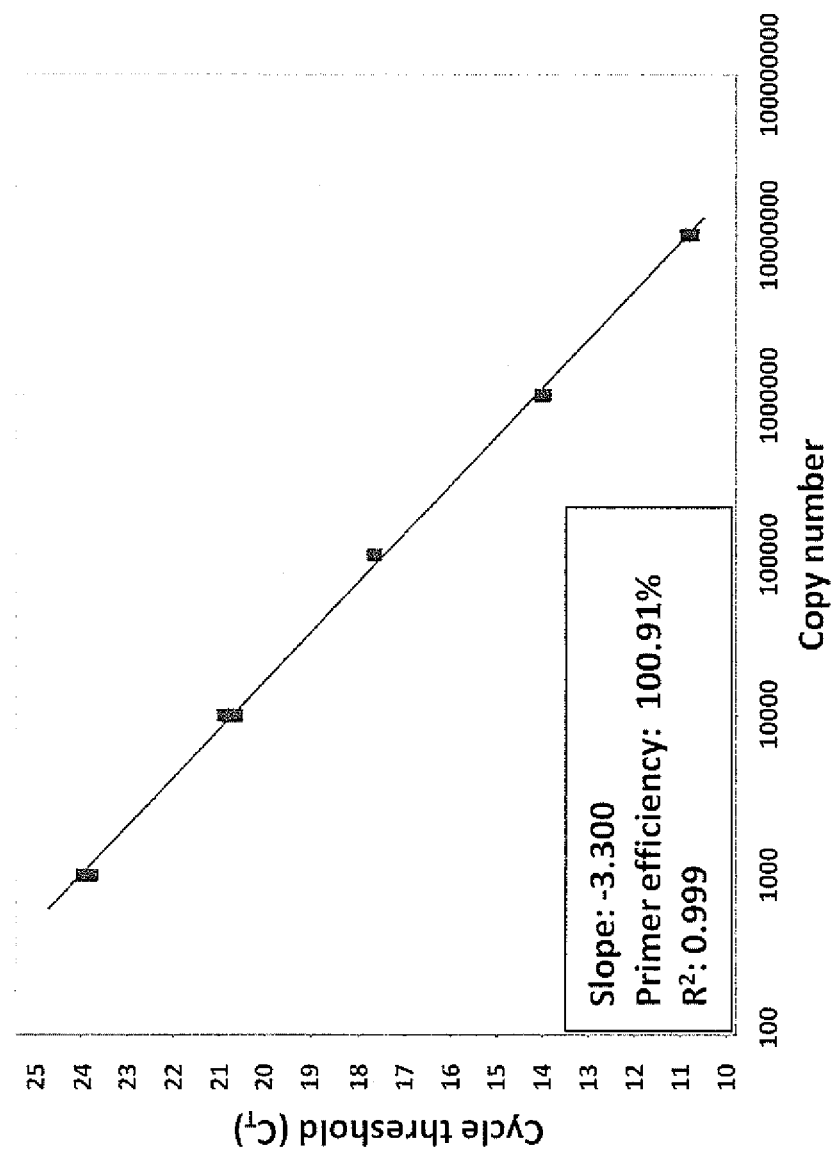
FIGS. 2C and 2D are molecular standard curves in water (FIG. 2C) and with approximately 50 ng levels of background Ca. L. *asiaticus* negative citrus DNA (FIG. 2D), showing the optimized efficiency of LJ900fr at approximately 100% and $R^2$ at approximately 0.999 for each.
Figure 2D:
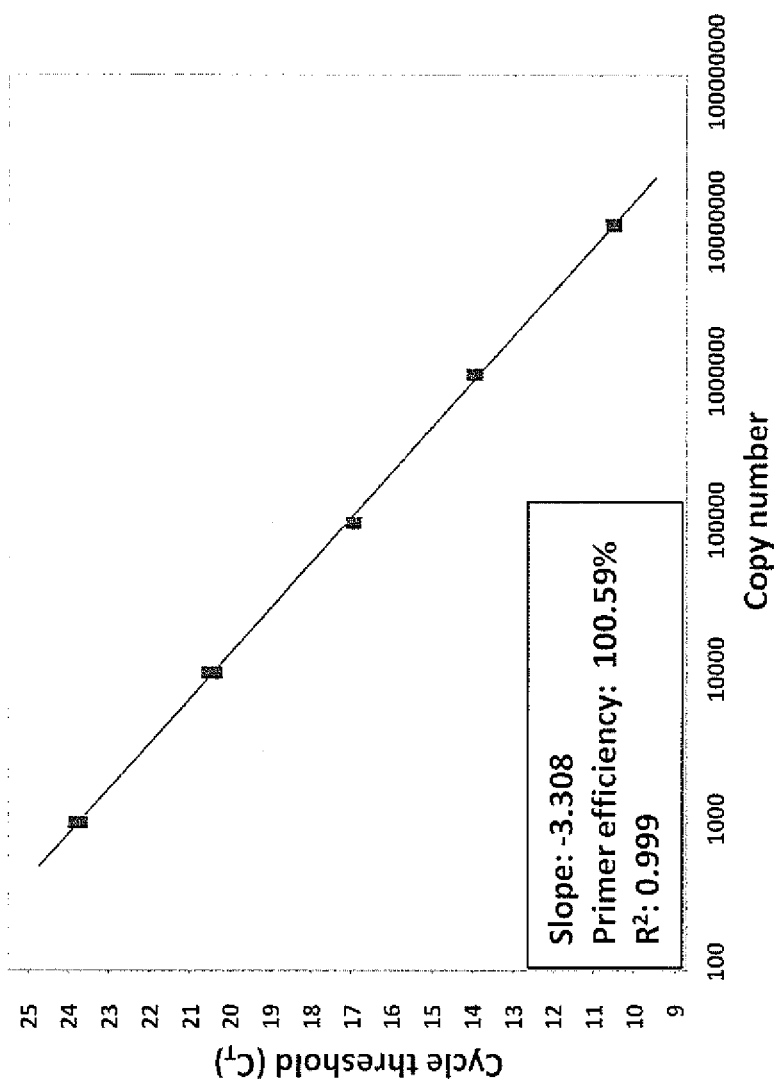

Additionally, as SG1 allows a subsequent melt analysis to validate amplicon fidelity, FIG. 2B demonstrates associated curve profiles of multiple sample well analyses for LJ900fr using Perfecta SYBR Green FastMix producing a mean melt peak at approximately 75 degrees C. The melt curve remained consistent with little or no variance regardless of variable background DNA levels. This provides additional support that spurious fluorescence from host DNA species was not a factor in SG1 detection using LJ900fr.

EXAMPLE 5

Total DNA extracts were isolated from midribs of citrus samples (Table 2 and Table 3) collected in the U.S. Horticulture Research Laboratory (USHRL) Picos Farm or USHRL maintained greenhouses in Fort Pierce, Fla., in accordance with standard DNeasy® Plant Mini Kit isolation protocols (Qiagen Inc., Valencia, Calif.). Midrib tissue samples were finely chopped, and approximately 0.2 g was placed into a sterilized 2 mL screw cap tube containing approximately two 4 mm Silicone-Carbide Sharp Particles and approximately four 2.3 mm Chrome-Steel Beads (BioSpec Products, Inc, Bartlesville, Okla.) on ice; approximately 800 µL of DNeasy® AP1 lysis buffer was added; and the tissues were homogenized by a FastPrep-24 System (MP Biomedicals, Solon, Ohio) for two successive rounds at approximately 6.5 M/S for approximately 45 seconds. Subsequent steps followed pursuant with the DNeasy® Plant Mini Kit protocol (Qiagen) from the 'RNase A' step. Citrus DNA samples from the USDA National Clonal Germplasm Repository for Citrus and Dates in Riverside, Calif. were isolated using either Plant DNeasy or MagAttract® 96 DNA Plant mini-prep systems pursuant with manufacturer's directions (Qiagen). Samples representing different counties in Florida (Table) and local M. paniculata plants were processed using DNeasy® DNA isolation for plant samples as described. Global citrus DNA samples (Table 5) were received directly as total DNA extracts by collaborators using a CTAB (Murray and Thompson, Nucleic Acids Res., Volume 8, 4321-4325, 1980) method.

Psyllids, *Diaphorina citri*, (Table 6 and Table 2) were processed for total DNA using phenol/chloroform extraction as described by Hung, et al 2004 (Hung et al., Plant Pathology, Volume 53, 96-102, 2004). DNA from bacterial strains: *X. citri* subsp. *citri* (Citrus Canker agent), *X. axonopodis* pv. *citrumelo* (agent of citrus bacterial spot), *R. solanacearum* (multi-host bacterial plant pathogen), and *E. coli* DH5α was isolated using the Promega Wizard® Genomic DNA Purification Kit (Promega Corporation, Madison, Wis.) in accordance with manufacturers' protocols. Total soil DNA extracts were isolated from approximately 1 g of soil/dirt in approximately 9 mL of approximately 1×PBS buffer that was vigorously vortexed for about 1 minute and approximately 1 mL aliquot was transferred to a sterile 1.5 mL micro-centrifuge tube and centrifuged at a low speed of approximately 1,000×g for about 10 minutes to pellet soil debris. Supernatant was transferred to a new sterile 1.5 mL micro-centrifuge tube and centrifuged at a high speed of approximately 20,000×g for about 10 minutes to pellet bacteria. Total DNA extracted from the bacterial pellet was processed using the Promega Wizard® Genomic DNA Purification Kit (Promega) in accordance with manufacturer's protocols. All DNA extracts were stored at approximately −80 degrees C. for use.

Comparisons between LJ900fr (SYBR Green I), LJ900fpr (TaqMan®), and HLBaspr (standard 16S rDNA-based TaqMan® 'Ca. L. asiaticus' detection) protocols with a standardized (equal samples and quantities tested) sample set (Table 3) were performed. 'Ca. L. asiaticus' bacterium was detected by all three methods in 18 of 29 samples (Table 3). By single factor ANOVA, significant differences (P<0.05) existed for cycle threshold detection between LJ900fr compared with LJ900fpr with $P=3.9\times10^{-4}$ and LJ900fr relative to HLBaspr with $P=7.7\times10^{-7}$. In Table 3, the average Ct difference between LJ900fr compared with these was approximately −3.71 (St. dev.±1.16) and −9.81 (St. dev.±1.02) Ct's for LJ900fpr and HLBaspr methods, respectively. Additionally, significant difference (P<0.05) existed between LJ900fpr and HLBaspr methods with $P=4.1\times10^{-2}$ in comparative samples.

The STDP method showed no significant difference (P>0.05, P=0.993) to LJ900fr in 'Ca. L. asiaticus' detection for samples: 1, 3-8, 13, and 26-28; however, STDP did not return a detectable signal (data not shown), for samples 2, 14-20, 23-25, and 29 where conversely LJ900fr and LJ900fpr returned average Ct's of 27.46 and 33.92, respectively.

Ten-fold serial dilution of a 'Ca. L. asiaticus' positive citrus sample 'VPCQ' were comparatively tested by LJ900fr, LJ900fpr, and HLBaspr methods (Table). From approximately $10^{-1}$ to $10^{-4}$ dilutions, each method detected the presence of 'Ca. L. asiaticus'. At approximately $10^{-5}$, only LJ900fr and LJ900fpr were capable of detecting 'Ca. L. asiaticus'. At approximately $10^{-6}$ and beyond, only LJ900fr was able to detect 'Ca. L. asiaticus'. For approximately $10^{-8}$, none of these methods was capable of detecting 'Ca. L. asiaticus', indicating the reliability of low level target detection by LJ900 methods compared with HLBaspr.

Figures 3A, 3B:
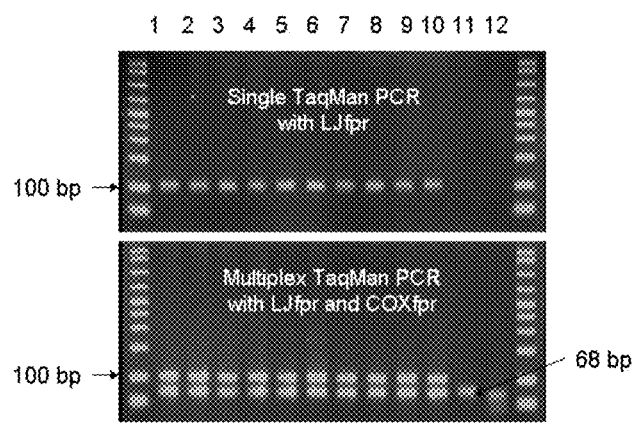
FIGS. 3A and 3B are photographs of a 2.5% agarose gel image of singleplex LJ900fr (FIG. 3A) and multiplex LJ900fpr with COXfrp (FIG. 3B) indicating amplicon products of single 100 bp (LJ900fpr) or 68 bp (COXfpr) bands. Lanes 11 and 12 (FIG. 3A and FIG. 3B gels) are Ca. L. *asiaticus* negative citrus controls.

COXfpr, a primer/probe set targeting the plant cytochrome oxidase, provides a reliable positive internal control targeting host plant DNA when used in multiplex real-time PCR (Li et al., 2006, supra). As shown in FIG. 3 lower gel, LJ900fpr (TaqMan®) was used in multiplex real-time PCR in combination with the COXfpr primer/probe set (Table 1). As expected, the COXfpr produced a band of approximately 68 bp while LJ900fpr produced a band of approximately 100 bp (FIG. 3). Neither PCR amplification efficiency, nor specificity relative to standard singleplex real-time PCR with LJ900fpr was affected by the multiplexing reaction (data not shown).

A comparison of multiplex reactions using the internal plant control COXfpr with LJ900fpr or HLBaspr in multiplex reactions indicated no significant differences of COXfpr Ct values (Table 5). Consistent with the singleplex results of Table 3, LJ900fpr (in multiplex) yielded significantly different Ct values for 'Ca. L. asiaticus' compared with HLBaspr for 15 DNA extracts from HLB suspects of field-grown sweet orange trees from 15 counties in Florida. Thirteen DNA extracts yielded lower Ct values for LJ900fpr than for HLBaspr, while two DNA extracts (#8 and #12) produced higher Ct values for LJ900fpr than for HLBaspr. This detection inconsistency may result from reduced numbers of tandem-repeat quantity per cell in the 'Ca. L. asiaticus' populations within these samples. Sample #13 tested negative for 'Ca. L. asiaticus' using HLBaspr but yielded a high Ct of approximately 37.59 using LJ900fpr.

To evaluate the potential of LJ900 primers in worldwide *Liberibacter* detection, globally derived DNA samples, including psyllid and citrus varieties from HLB infected regions of Brazil, China, the Philippines, India, and Thailand were tested. Table 6 indicates detection of *Liberibacter* within these samples by LJ900fr. Additionally, tests from alternate 'Ca. L. asiaticus' infected hosts including periwinkle, dodder, and orange jasmine (*Murraya paniculata*) were performed. Positive detection of 'Ca. L. asiaticus' in these samples indicated the presence of the hyvI/hyvII repeats in all DNA isolates of various origins and hosts evaluated (Table 6, or data not shown).

To investigate the presence of the hyvI/hyvII repeat sequence in other species of 'Ca. *Liberibacter*' (*americanus* and *africanus*), DNA samples from Brazil and South Africa were analyzed using LJ900fr in comparison with standard 'Ca. L. americanus or africanus' real-time PCR protocols: HLBampr and rplJAm for 'Ca. L. americanus', HLBafpr for 'Ca. L. africanus'(Teixeira et al, 2008, supra; Li et al., 2006, supra). In addition to LJ900fr analysis, the use of alternate 'Ca. L. asiaticus' detection methods HLBaspr, STDP, and rplLAs (Teixeria et al., 2008, supra; Li et al., 2006, supra; Lin et al, 2010, supra) were performed to aid in differentiating mixed *Liberibacter* populations. As shown in Table 6, Brazilian samples tested positive for hyvI/hyvII by LJ900fr. To determine the *Liberibacter* populations within these samples, the primer/probe sets rplJAm and HLBampr specific to 'Ca. L americanus' and those specific to 'Ca. L. asiaticus' rplLAs, STDP, and HLBaspr were used. For these samples, Psy-Br12, Psy-Br17, Brazil-Amer.11, Ct values of 32.98, 21.74, 21.70 and 37.51, 25.35, 26.34 by rplJAm and HLBampr were obtained respectively; however, no detectable Ct values were observed by 'Ca. L. asiaticus' methods rplLAs, STDP, and HLBaspr (data not shown). These data indicated that samples Psy-Br12, Psy-Br17, and Brazil-Amer.11 contained exclusive 'Ca. L. americanus' populations and that the presence of the hyvI/hyvII repeat was indicated. The Brazil 'AM' citrus sample (Table 6, sample #4) indicated a mixed population of 'Ca. L. americanus' and 'Ca. L. asiaticus' by these same real-time methods (data not shown).

The investigation of 'hyvI/hyvII-like' repeat sequence within 'Ca. L. africanus' was limited to a single African sample—'Laf 2'. The presence 'Ca. L. africanus' within 'Laf 2' sample was confirmed by HLBafpr having a Ct value of 23.77 (St. dev.±0.13); however, repeated LJ900fr tests failed to produce positive amplification for the hyvI/hyvII sequence, indicating that the hyvI/hyvII repeat region was either lacking or of a variant sequence type within the 'Ca. L. africanus' 'Laf 2' sample.

Citrus seedlings grown from seeds derived from previously positive HLB citrus varieties including: pomelo, trifoliate, grapefruit, and sweet orange along with USHRL reared 'Ca. L. asiaticus' free psyllids (D. citri) fed solely upon these seedlings, were tested for the presence of the hyvI/hyvII repeat by LJ900fr. Table 2 lists a representative sample set from these seedling or seedling fed psyllids, indicating detection by LJ900fr for the hyvI/hyvII repeat ranging from approximately 23 to no detectable cycle threshold.

The addition of an internal probe to forward and reverse primer pairs for real-time PCR is considered to provide greater amplicon specificity relative to non-probe based methods. To determine the relative detection of the LJ900fpr, a comparative analysis of selected samples (Table 3) with LJ900fpr verses LJ900fr and HLBaspr methods was performed. LJ900fpr returned an average 3.71 (St. dev.±1.04) Ct's earlier than HLBaspr yet it was on average 6.27 (St. dev.±1.04) Ct's later in detection than LJ900fr for these samples (Table 3).

To determine the SYBR Green 1 effect in-lieu-of the TaqMan® probe (HLBp) of HLBaspr, SG1 was substituted into the reaction for analysis of Table 3 samples 6, 10, and 11. An average ΔCT (HLBasr/SG1-HLBaspr) of −4.29 (St. dev.±0.13) reduction (earlier detection) in cycle threshold detection was obtained when SG1 was substituted for the TaqMan® probe, indicating a significant reduction/earlier cycle detection using SYBR Green 1 in these primers in-lieu-of the TaqMan HLBp probe for these samples. Further testing of HLBasr/SG1 with HLBaspr undetectable Table 3 samples 17, 18, and 20, resulted in a mean cycle threshold detection of 35.51 (St. dev.±0.39) for sample 17; while samples 18 and 20 remained non-detectable even by HLBasr/SG1.

Figure 4:
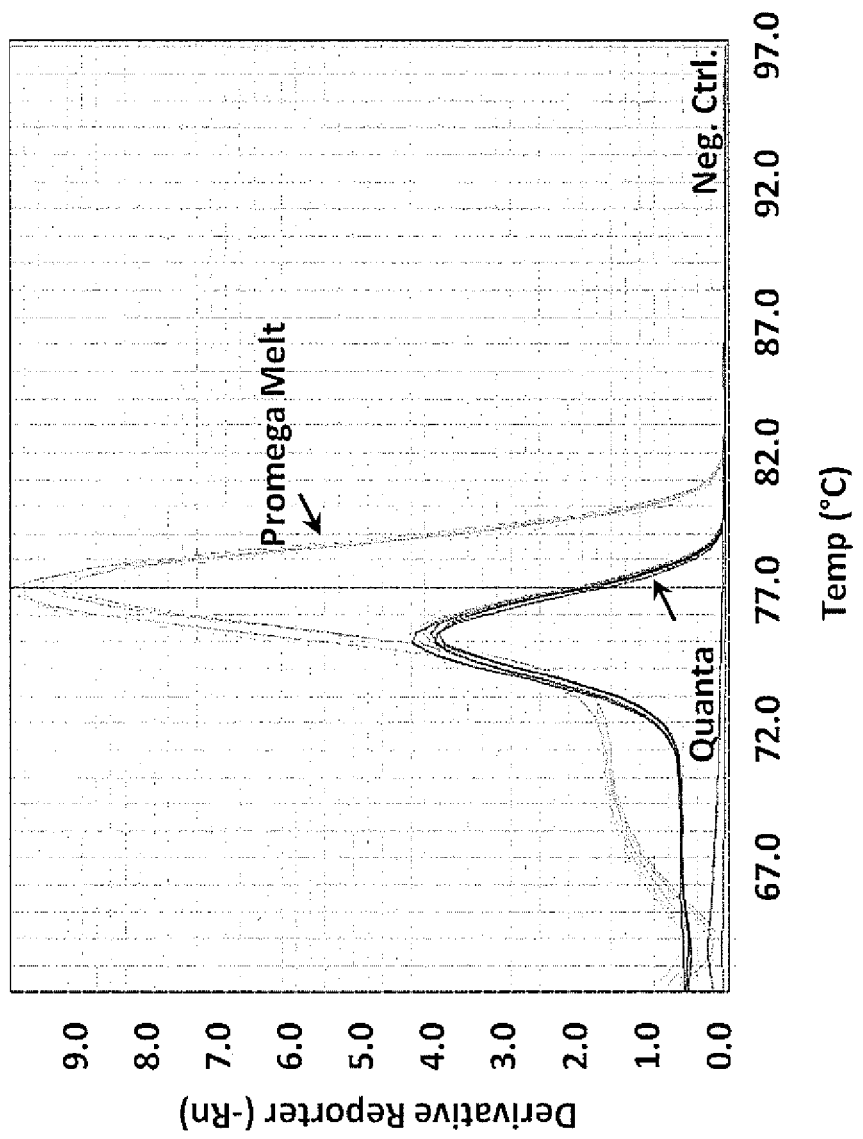
FIG. 4 is a graph showing equivalent sample melt curve analyses using GoTaq® real-time PCR Master Mix (Promega) and Perfecta™ SYBR® Green FastMix™ (Quanta) 2× master mixes using ABI Fast 7500 real-time PCR system, indicating the relative intensity of the Promega melt peak being more than twice that of the Quanta.

As the proprietary contents of commercial master mixes vary in formulation from one company to another, a comparison was made with respect to LJ900fr using two alternate mixes. Testing of pLJ153.1 at dilutions of $10^5$ to $10^3$ with the Promega GoTaq® real-time PCR master mix verses the PerfeCTa SYBR Green FastMix from Quanta Biosciences under the same conditions (on the same plate) indicated a statistically significant difference in detection levels by these master mixes. The GoTaq® at $10^5$, $10^4$, and $10^3$ dilutions returned Ct's of: 16.83 (St. dev.±0.09), 20.32 (St. dev.±0.07), and 24.28 (St. dev.±0.05), respectively. Quanta FastMix returned Ct's of: 16.53 (St. dev.±0.13), 19.85 (St. dev.±0.10), and 23.32 (St. dev.±0.30) for these same sample dilutions. Single factor ANOVA at 95% confidence interval returned a statistically significant difference between these mixes (P<0.05) at each dilution ($10^5$ at P=8.0×$10^{-3}$, $10^4$ at P=6.6×$10^{-6}$, and $10^3$ at P=7.4×$10^{-5}$, respectively) with the Quanta returning the lowest detectable thresholds under these conditions. However, the Promega GoTaq melt curve analyses indicated a greater than 2× derivative reporter (−Rn) value relative to the same melt analyses of the Quanta FastMix comparative samples (FIG. 4), a potentially useful attribute for high-resolution melt analyses applications.

TABLE 4

Real-time PCR comparison of 'Ca. L. asiaticus' dilution sample detection by LJ900fr, LJ900fpr, and HLBaspr methods

| Sample 'VPCQ' Dilutions | Mean Ct value by Method (±St. dev. Mean Ct) | | |
|---|---|---|---|
| | LJ900fr Ct | LJ900fpr Ct | HLBaspr Ct |
| $10^{-1}$ | 15.90 (±0.05) | 21.65 (±0.38) | 25.64 (±0.06) |
| $10^{-2}$ | 19.30 (±0.09) | 24.93 (±0.07) | 28.88 (±0.08) |
| $10^{-3}$ | 22.94 (±0.06) | 29.11 (±0.02) | 32.29 (±0.05) |
| $10^{-4}$ | 26.00 (±0.03) | 32.67 (±0.21) | 34.98 (±0.08) |
| $10^{-5}$ | 28.78 (±0.10) | 35.72 (±0.29) | ND |
| $10^{-6}$ | 32.70 (±0.23) | ND | ND |
| $10^{-7}$ | +/− | ND | ND |
| $10^{-8}$ | ND | ND | ND |

ND = No Detection
+/− = Greater than 50% amplification detected within replicates but less than 100% positive

TABLE 5

Comparison of multiplex TaqMan real-time PCR based on hyvI/hyvII repeat and 16S rDNA genes of 'Ca. L. asiaticus'

| [a]Florida Citrus Sample | TaqMan qPCR Ct | | 16S rDNA TaqMan qPCR Ct | |
|---|---|---|---|---|
| | LJ900fpr | [b]COXfpr | HLBaspr | [b]COXfpr |
| 1 | 20.71 | 18.12 | 24.93 | 18.46 |
| 2 | 19.67 | 17.50 | 23.69 | 17.77 |
| 3 | 18.72 | 17.77 | 22.15 | 17.59 |
| 4 | 19.99 | 16.81 | 22.32 | 17.28 |
| 5 | 20.26 | 20.18 | 22.16 | 20.30 |
| 6 | 17.86 | 17.93 | 22.18 | 18.16 |
| 7 | 23.44 | 19.51 | 25.83 | 20.07 |
| 8 | 39.05 | 17.59 | 34.89 | 17.70 |
| 9 | 20.43 | 18.26 | 23.50 | 18.36 |
| 10 | 22.40 | 18.72 | 25.19 | 18.62 |
| 11 | 36.50 | 18.92 | 37.12 | 18.74 |
| 12 | 38.71 | 17.72 | 34.03 | 17.42 |
| 13 | 37.59 | 18.20 | 0.00 | 19.30 |
| 14 | 23.36 | 18.46 | 27.07 | 18.57 |
| 15 | 37.28 | 19.53 | 39.54 | 19.17 |
| Mean Ct | 25.59 | 18.35 | 27.47 | 18.50 |

[a]DNA extracts are from foliar midrib of HLB-symptomatic sweet orange trees from field in 15 counties of Florida
[b]The TaqMan primer/probe set COXfpr was based on plant cytochrome oxidase (COX)

TABLE 6

LJ900fr real-time PCR hyvI/hyvII repeat detection within citrus, psyllid, and Murraya hosts from global origins

| Host | Origin | Sample # | Name | Mean Ct value (±St. dev. Mean Ct) LJ900fr Ct |
|---|---|---|---|---|
| Psyllid (D. citri) | Brazil | 1 | [a]Psy-Br12 | 17.41 |
| Psyllid (D. citri) | Brazil | 2 | [a]Psy-Br17 | 19.13 |
| Psyllid (D. citri) | Brazil | 3 | [a]Brazil-Amer.11 | 27.82 |
| Citrus | Brazil | 4 | Brazil 'AM' | 23.33 (±0.15) |
| Tangerine | Fujian, China | 5 | C18-CH | 17.14 (±0.17) |
| Tangerine | Fujian, China | 6 | C2-CH | 22.09 (±2.01) |

TABLE 6-continued

LJ900fr real-time PCR hyvI/hyvII repeat detection within citrus, psyllid, and Murraya hosts from global origins

| Host | Origin | # | Sample Name | Mean Ct value (±St. dev. Mean Ct) LJ900fr Ct |
|---|---|---|---|---|
| Kumquat | Fujian, China | 7 | C3-CH | 23.71 (±0.09) |
| Citrus | Fujian, China | 8 | Cha12 | 21.37 (±2.86) |
| Psyllid (*D. citri*) | Fujian, China | 9 | [a]Ch.Psy1-1 | 28.28 |
| Psyllid (*D. citri*) | Fujian, China | 10 | Ch.Psy1-10 | 18.69 (±1.14) |
| Psyllid (*D. citri*) | Fujian, China | 11 | [a]Ch.Psy1-2 | 22.31 |
| Psyllid (*D. citri*) | Philippines | 12 | F3957.1 | 18.84 (±0.02) |
| Psyllid (*D. citri*) | Philippines | 13 | F3957.18 | 11.91 (±7.83) |
| Psyllid (*D. citri*) | Philippines | 14 | F3957.2 | 14.80 (±0.74) |
| Psyllid (*D. citri*) | Philippines | 15 | F3957.21 | 19.82 (±0.27) |
| Psyllid (*D. citri*) | Philippines | 16 | F3957.4 | 10.58 (±0.97) |
| Citrus | India | 17 | [a]#25 | 20.91 |
| Citrus | India | 18 | #17 | 30.74 (±0.12) |
| Citrus | India | 19 | #18 | 28.86 (±0.50) |
| Psyllid (*D. citri*) | India | 20 | 01.01.10 #1 | 18.82 (±0.16) |
| Psyllid (*D. citri*) | India | 21 | 01.01.10 #2 | 19.53 (±0.38) |
| Tangerine | Thailand | 22 | 08.14.09.2 | 11.41 (±5.52) |
| Psyllid (*D. citri*) | Thailand | 23 | [a]Thai Psy.2 | 25.49 |
| Psyllid (*D. citri*) | Thailand | 24 | [a]Thai Psy.4 | 24.64 |
| Psyllid (*D. citri*) | Thailand | 25 | [a]Thai Psy.26 | 21.50 |
| Psyllid (*D. citri*) | Thailand | 26 | [a]Thai Psy.28 | 25.54 |
| Psyllid (*D. citri*) | Thailand | 27 | [a]Thai Psy.32 | 24.69 |
| Psyllid (*D. citri*) | Thailand | 28 | [a]Thai Psy.38 | 24.86 |
| Psyllid (*D. citri*) | Thailand | 29 | [a]Thai Psy.39 | 24.95 |
| Psyllid (*D. citri*) | Thailand | 30 | [a]Thai Psy.41 | 25.15 |
| Murraya (*M. paniculata*) | Florida, USA | 31 | M3 | 33.12 (±0.55) |
| Murraya (*M. paniculata*) | Florida, USA | 32 | M14 | 33.61 (±1.76) |
| Murraya (*M. paniculata*) | Florida, USA | 33 | M16 | 33.06 (±0.33) |
| Murraya (*M. paniculata*) | Florida, USA | 34 | M62 | 32.55 (±1.90) |

[a]Insufficient DNA quantities precluding technical replicates, therefore no St. Dev. is reported

TABLE 7A

Real-time PCR

| | 15 uL reaction | | 15 uL reaction |
|---|---|---|---|
| Perfect SYBR Fastmx (2X) | 7.5 | TaqMan (2X) | 7.5 |
| LJ900f (6 µM) | 1.5 | LJ900f (6 µM) | 1.65 |
| LJ900r (9 µM) | 1.5 | LJ900r (9 µM) | 1.65 |
| DNA * | 1-2 | LJ900p (5 µM) | 1.65 |
| H$_2$O | To the volume of 15 | DNA * | 1-2 |
| | | H$_2$O | To the volume of 15 |

Perfect SYBR fastmx order from Quanta Biosciences via VWR (Cat: 101414-288, LRX 5000)
TaqMan ® Fast Universal PCR Master Mix (2x) order from ABI (Cat: 4352042 )
* if you use plasmid DNA as template, diluted first and use about 20 ng plasmid DNA in each reaction

TABLE 7B qPCR SYBR ® Green 15 µL total reaction components for LJ900 Series primers

| Reaction Components | General Information | Single reaction volume (15 µL total) | Single sample 1.1X[a] Correction | 96 Well Reaction Volumes (w/1.1X correction) |
|---|---|---|---|---|
| SYBR ® Green | 2x Master Mix | 7.50 µL | 8.25 µL | 792.0 µL |
| Forward Primer | 6 µM working stock | 1.50 µL | 1.65 µL | 158.4 µL |
| Reverse Primer | 9 µM working stock | 1.50 µL | 1.65 µL | 158.4 µL |
| H$_2$O | Pure/Nuclease free | 2.50 µL | [b,c]2.95 µL | 283.2 µL |
| Template | e.g. gDNA, cDNA, etc | 2.00 µL | [b,d]2.00 µL | Variable (2.0 µL per well) |

[a]1.1X correction to compensate for pipette tip liquid retention, excess allows for enough reagents to ensure full reaction coverage with minimal overrun
[b]Volume is dependent upon user, for example H$_2$O varies depending upon DNA volume per reaction
[c]1.1X H$_2$O correction includes added 0.2 µL from DNA, (2.5 × 1.1 = 2.75 + 0.2 [from DNA correction] = 2.95 µL)
[d]DNA to remain at constant final volume without additional correction factor of +0.2 µL (2.0 × 1.1 = 2.2 µL)

All publications and patents mentioned in this specification are herein incorporated by reference to the same extent as if each individual publication or patent was specifically and individually indicated to be incorporated by reference.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

We claim:

1. A method for detecting the presence of *Candidatus Liberibacter* species in a plant or insect which may contain said *Candidatus Liberibacter* comprising:
    (a) exposing a nucleic acid to a first primer comprising the polynucleotide sequence of SEQ ID NO: 1, to a second primer comprising the polynucleotide sequence of SEQ ID NO: 2, and to a detector molecule, wherein said nucleic acid was isolated from a sample of tissue from a plant or insect capable of containing a *Candidatus Liberibacter* species;
    (b) amplifying said exposed nucleic acid using a DNA amplification method, and
    (c) quantifying the amplified nucleic acid by detection of said detector molecule.

2. The method of claim 1 wherein said detector molecule is a fluorescent reporter dye.

3. The method of claim 2 wherein said detector molecule is a DNA intercalation dye.

4. The method of claim 1 wherein said detector molecule comprising a fluorescent reporter dye, a quencher dye, and a probe comprising the polynucleotide sequence of SEQ ID NO: 3 or the reverse complement thereof, wherein said fluorescent reporter dye and said quencher dye are linked to said probe.

5. The method of claim 1 wherein said detector molecule comprising a fluorescent reporter dye, a quencher dye, and a probe comprising a polynucleotide sequence of at least 15 contiguous nucleotides in SEQ ID NO: 28 or SEQ ID NO: 29, wherein said fluorescent reporter dye and said quencher dye are linked to said probe.

6. A method for detecting the presence of Ca. *Liberibacter* species in a plant or insect host comprising:
    (a) exposing a nucleic acid to a first primer comprising the reverse complement polynucleotide sequence of SEQ ID NO: 1, to a second primer comprising the reverse complement polynucleotide sequence of SEQ ID NO: 2, and to a detector molecule, wherein said nucleic acid was isolated from a sample of tissue from a plant or insect capable of containing a *Candidatus Liberibacter* species;
    (b) amplifying said exposed nucleic acid using a DNA amplification method; and
    (c) quantifying the amplified nucleic acid by detection of said detector molecule, wherein said insect host is a psyllid.

7. The method of claim 6 wherein said detector molecule is a fluorescent reporter dye.

8. The method of claim 7 wherein said detector molecule is a DNA intercalation dye.

9. The method of claim 6 wherein said detector molecule comprising a fluorescent reporter dye, a quencher dye, and a probe comprising the polynucleotide sequence of SEQ ID NO: 3 or the reverse complement thereof, wherein said fluorescent reporter dye and said quencher dye are linked to said probe.

10. The method of claim 6 wherein said detector molecule comprising a fluorescent reporter dye, a quencher dye, and a probe comprising a polynucleotide sequence of at least 15 contiguous nucleotides in SEQ ID NO: 28 or SEQ ID NO: 29, wherein said fluorescent reporter dye and said quencher dye are linked to said probe.

* * * * *

SEQUENCE LISTING

```
<160> NUMBER OF SEQ ID NOS: 30

<210> SEQ ID NO 1
<211> LENGTH: 27
<212> TYPE: DNA
<213> ORGANISM: Candidatus Liberibacter asiaticus
<400> SEQUENCE: 1
gccgttttaa cacaaaagat gaatatc                                           27

<210> SEQ ID NO 2
<211> LENGTH: 27
<212> TYPE: DNA
<213> ORGANISM: Candidatus Liberibacter asiaticus
<400> SEQUENCE: 2
ataaatcaat ttgttctagt ttacgac                                           27

<210> SEQ ID NO 3
<211> LENGTH: 31
<212> TYPE: DNA
<213> ORGANISM: Candidatus Liberibacter asiaticus
<400> SEQUENCE: 3
acatctttcg tttgagtagc tagatcattg a                                      31

<210> SEQ ID NO 4
<211> LENGTH: 28
<212> TYPE: DNA
<213> ORGANISM: Candidatus Liberibacter asiaticus
<400> SEQUENCE: 4
cggtgaatgt attaagctga ggcgttcc                                          28

<210> SEQ ID NO 5
<211> LENGTH: 33
<212> TYPE: DNA
<213> ORGANISM: Candidatus Liberibacter asiaticus
<400> SEQUENCE: 5
acccacaaca aaatgagata caccaacaac ttc                                    33

<210> SEQ ID NO 6
<211> LENGTH: 20
<212> TYPE: DNA
<213> ORGANISM: Candidatus Liberibacter asiaticus
<400> SEQUENCE: 6
cgattggtgt tcttgtagcg                                                   20

<210> SEQ ID NO 7
<211> LENGTH: 23
<212> TYPE: DNA
<213> ORGANISM: Candidatus Liberibacter asiaticus
<400> SEQUENCE: 7
aacaatagaa ggatcaagca tct                                               23
```

<210> SEQ ID NO 8
<211> LENGTH: 28
<212> TYPE: DNA
<213> ORGANISM: Candidatus Liberibacter asiaticus

<400> SEQUENCE: 8
aatcaccgaa ggagaagcca gcattaca                                    28

<210> SEQ ID NO 9
<211> LENGTH: 20
<212> TYPE: DNA
<213> ORGANISM: Candidatus Liberibacter asiaticus

<400> SEQUENCE: 9
tcgagcgcgt atgcaatacg 20

<210> SEQ ID NO 10
<211> LENGTH: 24
<212> TYPE: DNA
<213> ORGANISM: Candidatus Liberibacter asiaticus

<400> SEQUENCE: 10
gcgttatccc gtagaaaaag gtag 24

<210> SEQ ID NO 11
<211> LENGTH: 18
<212> TYPE: DNA
<213> ORGANISM: Candidatus Liberibacter asiaticus

<400> SEQUENCE: 11
agacgggtga gtaacgcg 18

<210> SEQ ID NO 12
<211> LENGTH: 23
<212> TYPE: DNA
<213> ORGANISM: Candidatus Liberibacter asiaticus

<400> SEQUENCE: 12
cgagcgcgta ttttatacga gcg 23

<210> SEQ ID NO 13
<211> LENGTH: 21
<212> TYPE: DNA
<213> ORGANISM: Candidatus Liberibacter asiaticus

<400> SEQUENCE: 13
gagcgagtac gcaagtacta g 21

<210> SEQ ID NO 14
<211> LENGTH: 22
<212> TYPE: DNA
<213> ORGANISM: Candidatus Liberibacter asiaticus

<400> SEQUENCE: 14
gtatgccacg tcgcattcca ga 22

<210> SEQ ID NO 15
<211> LENGTH: 22
<212> TYPE: DNA
<213> ORGANISM: Candidatus Liberibacter asiaticus

<400> SEQUENCE: 15

-continued
gaatgccctt agcagttttg gc 22

<210> SEQ ID NO 16
<211> LENGTH: 19
<212> TYPE: DNA
<213> ORGANISM: Candidatus Liberibacter asiaticus
<400> SEQUENCE: 16
atccagatgc ttacgctgg 19

<210> SEQ ID NO 17
<211> LENGTH: 20
<212> TYPE: DNA
<213> ORGANISM: Candidatus Liberibacter asiaticus
<400> SEQUENCE: 17
actcctacgg gaggcagcag 20

<210> SEQ ID NO 18
<211> LENGTH: 17
<212> TYPE: DNA
<213> ORGANISM: Candidatus Liberibacter asiaticus
<400> SEQUENCE: 18
attaccgcgg ctgctgg 17

<210> SEQ ID NO 19
<211> LENGTH: 20
<212> TYPE: DNA
<213> ORGANISM: Candidatus Liberibacter asiaticus
<400> SEQUENCE: 19
tctacgratt tcaccyctac 20

<210> SEQ ID NO 20
<211> LENGTH: 26
<212> TYPE: DNA
<213> ORGANISM: Candidatus Liberibacter asiaticus
<400> SEQUENCE: 20
ggacaagggg atattggata atgatg 26

<210> SEQ ID NO 21
<211> LENGTH: 26
<212> TYPE: DNA
<213> ORGANISM: Candidatus Liberibacter asiaticus
<400> SEQUENCE: 21
attaagagtt ctaagcaacc tgacag 26

<210> SEQ ID NO 22
<211> LENGTH: 16
<212> TYPE: DNA
<213> ORGANISM: Candidatus Liberibacter asiaticus
<400> SEQUENCE: 22
cgcccgtttc cgttgt 16

<210> SEQ ID NO 23
<211> LENGTH: 23
<212> TYPE: DNA
<213> ORGANISM: Candidatus Liberibacter asiaticus

<400> SEQUENCE: 23

```
agcctcttta agccctaaat cag                                             23

<210> SEQ ID NO 24
<211> LENGTH: 1164
<212> TYPE: DNA
<213> ORGANISM: Candidatus Liberibacter asiaticus

<400> SEQUENCE: 24
atgattagaa aagtaaacat ggaaaaacta aacttcgaac aaactaaatc ggttacctat      60
tgggctgtag gatcaaagtt tgtcattcct tgggatatta aagatccaag taggattcat     120
gctgaagttg gatattccga tggaagagtt caagaactag caatatccca agattttgat     180
gtcgatgggt taaacgcttt gctaactgtc aacaatagag aaggggattt tatccgtatt     240
ttcgaaggtg agaaacaaac ttttaaagaa tataactctg atagccccag agctcctcat     300
aatcttgtta aagaagcgga tttgtatcct ttgcataata gattagatgg tgttgaaact     360
atcgtttctg atcttaacaa tatgaaaaac aggatccaag aactagaaca aattgattta     420
tctaaactag aacaaattga tttatctgaa atggccgttt taacacaaaa gatgaatatc     480
gtagatggaa gagtcaatga tctagctact caaacgaaag atgttggtcg taaactagaa     540
caaattgatt tatctaaact agaaggttta gatccacaaa cacgaaagta tctacaagat     600
atacaaacgc agttaacgtc ggatacgctc acgcttcaac atgaggacac tagaaggtat     660
gcttcatcta taagtttcaa gggtaacgat ggggcactag ttggttggat cacgagagag     720
gttatagggg atcttaaggg tctatccata gcaacaaaga atcagagcgg aagccttgta     780
aatagtgtta aactctatga caacatggat gtctatatcc aaggtcagtg tttcattagg     840
ggaactgata cctctatctt tgatgaaata aaacgacaac taaaacctta tattctaggt     900
ttgctccaag ggcgtacaat ggtacgaagt gccaatctac gtgaaaaagc ttcaattggt     960
gatataataa caggggataa aatagactat tgggcttatc cttcagaaaa cggcagtggt    1020
tatatatcag ctagtgctac tcaagcacac acaatggcag ttagtgcaga agacgcacgt    1080
aaaagatgga ggattatggg tataactaga agttattact acacagggta ttggttacaa    1140
gaagttatta attttgatga ctaa                                           1164

<210> SEQ ID NO 25
<211> LENGTH: 2760
<212> TYPE: DNA
<213> ORGANISM: Candidatus Liberibacter asiaticus
<400> SEQUENCE: 25
atgattagaa aagtaaacat ggaaaaacta aacttcgaac aaactaaatc ggttacctat      60
tgggctgtag gatcaaagtt tgtcattcct tgggatatta aagatccaag taggattcat     120
gctgaagttg gatattccga tggaagagtt caagaactag caatatccca agattttgat     180
gtcgatgggt taaacgcttt gctaactgtc aacaatagag aaggggattt tatccgtatt     240
ttcgaaggtg agaaacaaac ttttaaagaa tataactctg atagccccag agctcctcat     300
aatcttgtta aagaagcgga tttgtatcct ttgcataata gattagatgg tgttgaaact     360
atcgtttctg atcttaacaa tatgaaaaac aggatccaag aactagaaca aattgattta     420
tctaaactag aacaaattga tttatctaaa atggccgttt taacacaaaa gatgaatatc     480
atagatgggg tagtcaagga tctagctact caaacgaaag atgttggtcg taaactagaa     540
caaattgatg tatctaaact agaacaaatt gatttatcta aaatggccgt tttaacacaa     600
```

| | |
|---|---|
| aagatgaata tcgtagatgg aagagtcaat gatctagcta ctcaaacgaa agatgttggt | 660 |
| cgtaaactag aacaaattga tttatctaaa ctagaacaaa ttgatttatc tgaaatggcc | 720 |
| gttttaacac aaaagatgaa tatcatagat gggatagtca ataatctagc tactcaaacg | 780 |
| gaagatgttg gtcgtaaact agaacaaatt gatttatcta aactagaaca aattgattta | 840 |
| tctgaaatgg ccgttttaac acaaaagatg aatatcatag atgggatagt caataatcta | 900 |
| gctactcaaa cggaagatgt tggtcgtaaa ctagaacaaa ttgatttatc taaactagaa | 960 |
| caaattgatt tatctgaaat ggccgtttta acacaaaaga tgaatatcat agatgggata | 1020 |
| gtcaataatc tagctactca acgaaagat gttggtcgta aactagaaca aattgattta | 1080 |
| tctaaactag aacaaattga tttatctgaa atggccgttt taacacaaaa gatgaatatc | 1140 |
| atagatggga tagtcaataa tctagctact caaacgaaag atgttggtcg taaactagaa | 1200 |
| caaattgatt tatctaaact agaacaaatt gattatctca aactagaaca aattgattta | 1260 |
| tctaaactag aacaaattga tttatctgaa atggccgttt taacacaaaa gatgaatatc | 1320 |
| atagatggga tagtcaatga tctagctact caaacggaag ttgttggtcg taaactagaa | 1380 |
| caaattgatt tatctaaact agaacaaatt gatttatctg aaatggccgt tttaacacaa | 1440 |
| aagatgaata tcatagatgg gatagtcaat aatctagcta ctcaaacgaa agatgttggt | 1500 |
| cgtaaactag aacaaattga tttatctaaa ctagaacaaa ttgatttatc taaactagaa | 1560 |
| caaattgatt tatctaaact agaacaaatt gatttatctg aaatggccgt tttaacacaa | 1620 |
| aagatgaata tcatagatgg gatagtcaat gatctagcta ctcaaacgga agttgttggt | 1680 |
| tgtaaactag aacaaattga tttatctaaa ctagaacaaa ttgatttatc tgaaatggcc | 1740 |
| gttttaacac aaaagatgaa tatcatagat gggatagtca ataatctagc tactcaaacg | 1800 |
| aaagatgttg gtcgtaaact agaacaaatt gatttatcta aactagaaca aattgattta | 1860 |
| tctaaactag aacaaattga tttatctaaa ctagaacgaa ttgatttatc tgaaatggcc | 1920 |
| gttttaacac aaaagatgaa tatcgtagat ggaatagtca atgatctagc tactcaaacg | 1980 |
| gaagttgttg gtcgtaagct agaacaaatt gatttatcta aactagaaca aattgattta | 2040 |
| tctgaaatgg ccgttttaac acaaaagatg aatatcgtag atggaagagt caatgatcta | 2100 |
| gctactcaaa cgaaagatgt tggtcgtaaa ctagaacaaa ttgatttatc taaactagaa | 2160 |
| ggtttagatc cacaaacacg aaagtatcta caagatatac aaacgcagtt aacgtcggat | 2220 |
| acgctcacgc ttcaacatga ggacactaga aggtatgctt catctataag tttcaagggt | 2280 |
| aacgatgggg cactagttgg ttggatcacg agagaggtta tagggatct taagggtcta | 2340 |
| tccatagcaa caaagaatca gagcggaagc cttgtaaata gtgttaaact ctatgacaac | 2400 |
| atggatgtct atatccaagg tcagtgtttc attaggggaa ctgatacctc tatctttgat | 2460 |
| gaaataaaac gacaactaaa accttatatt ctaggtttgc tccaagggcg tacaatggta | 2520 |
| cgaagtgcca atctacgtga aaagcttca attggtgata taataacagg gataaaata | 2580 |
| gactattggg cttatccttc agaaaacggc agtggttata tatcagctag tgctactcaa | 2640 |
| gcacacacaa tggcagttag tgcagaagac gcacgtaaaa gatggaggat tatgggtata | 2700 |
| actagaagtt attactacac agggtattgg ttacaagaag ttattaattt tgatgactaa | 2760 |

<210> SEQ ID NO 26
<211> LENGTH: 120
<212> TYPE: DNA
<213> ORGANISM: Candidatus Liberibacter asiaticus

<400> SEQUENCE: 26

```
gccgttttaa cacaaaagat gaatatcgta gatggaagag tcaatgatct agctactcaa    60
cggcaaaatt gtgttttcta cttatagcat ctaccttctc agttactaga tcgatgagtt   120
```

<210> SEQ ID NO 27
<211> LENGTH: 80
<212> TYPE: DNA
<213> ORGANISM: Candidatus Liberibacter asiaticus

<400> SEQUENCE: 27
acgaaagatg ttggtcgtaa actagaacaa attgatttat tgctttctac aaccagcatt 60
tgatcttgtt taactaaata 80

<210> SEQ ID NO 28
<211> LENGTH: 100
<212> TYPE: DNA
<213> ORGANISM: Candidatus Liberibacter asiaticus

<400> SEQUENCE: 28
gccgttttaa cacaaaagat gaatatcgta gatggaagag tcaatgatct agctactcaa 60
acgaaagatg ttggtcgtaa actagaacaa attgatttat 100

<210> SEQ ID NO 29
<211> LENGTH: 100
<212> TYPE: DNA
<213> ORGANISM: Candidatus Liberibacter asiaticus

<400> SEQUENCE: 29
ataaatcaat ttgttctagt ttacgaccaa catctttcgt ttgagtagct agatcattga 60
ctcttccatc tacgatattc atcttttgtg ttaaaacggc 100

<210> SEQ ID NO 30
<211> LENGTH: 1026
<212> TYPE: DNA
<213> ORGANISM: Candidatus Liberibacter asiaticus

<400> SEQUENCE: 30
atgatgcaat ataacttcga gcaatcgaaa gatgtgtctt atcgtctttt tggctcttat 60
tttgttattc cttggactgt taaagatcca agtaggattc atgctgaagt taaatatcct 120
gatggcaaca tggaagaatt aagtcctgaa agagatttta aagttgatgt agacgaaagc 180
agtttgattt taagttctaa aaggtggatt aacaataata acgctttaag gattttcgaa 240
ggtgagaaac aaacttttaa agattttaac atagaggtac aaaagaaagt aaatcaggta 300
aacgttttaa cacaaaagat gaataccata gatgggatag tcaatgatct agctattcaa 360
acggaagatg ttggtcgtaa actagaacaa attgatttat ctaaagtaga aggtttagat 420
ccacaaacac gaaagtatct acaagatata caaacgcagt taacgtcgga tacgctcacg 480
cttcaacttg atgacactag agttgatgac actagagggt atgattcatc tatacgtttc 540
aaggataaag atggggcact aggtggttcg atcacgagag tggttaaagg ggatattacg 600
ggtctatcta tagcaacaaa gaataagagc ggaagccttg aaaatcgtat taaattctat 660
gacgacaagg atgtttatat caacggtcag tgcttcgtta agggaacgga tacctctatc 720
tttgatgaaa tagcacgaca actaacacct cgttttctag gtttgctcca aggtcgtaca 780
atggtacgaa gtgccaatct acgtgaaaaa gcttcaattg gtgatataat aacaggggat 840
aaaatagcct attgggctta tccttcagaa aacagcagtg gttatatatc agctagtgct 900

-continued

```
actcaagaac acacaatggc agttagtgca gaaaacgcac gtaaaagatg gaggattatg    960
ggtaaaactg acagttatta catcacactg tattggttac aagaagttat taattttgat   1020
gactaa                                                              1026
```